United States Patent [19]

Kotidis et al.

[11] Patent Number: 5,604,592
[45] Date of Patent: Feb. 18, 1997

[54] LASER ULTRASONICS-BASED MATERIAL ANALYSIS SYSTEM AND METHOD USING MATCHED FILTER PROCESSING

[75] Inventors: Petros A. Kotidis, Framingham; James F. Cunningham, Lincoln; Paul F. Gozewski, Haverhill; Charles Borsody, Winchester; Daniel E. Klimek, Lexington; Jaime A. Woodroffe, North Reading, all of Mass.

[73] Assignee: Textron Defense Systems, Division of Avco Corporation, Wilmington, Mass.

[21] Appl. No.: 482,782

[22] Filed: Jun. 7, 1995

Related U.S. Application Data

[62] Division of Ser. No. 308,372, Sep. 19, 1994.
[51] Int. Cl.$^6$ .............................. G01B 9/02; G01N 21/00
[52] U.S. Cl. ........................................... 356/357; 356/432
[58] Field of Search ............................... 356/357, 432; 73/655, 657

[56] References Cited

U.S. PATENT DOCUMENTS

| | | |
|---|---|---|
| Re. 34,604 | 5/1994 | Shaw . |
| 3,601,490 | 8/1971 | Erickson . |
| 3,694,088 | 9/1972 | Gallagher et al. . |
| 3,885,224 | 5/1975 | Klahr . |
| 3,978,713 | 7/1976 | Penney . |
| 4,052,889 | 10/1977 | Mucciardi et al. . |
| 4,144,753 | 3/1979 | Larsen . |
| 4,144,767 | 3/1979 | Kaule et al. . |
| 4,201,473 | 5/1980 | Domenicali et al. . |
| 4,225,240 | 9/1980 | Balasubramanian . |
| 4,255,971 | 3/1981 | Rosencwaig . |
| 4,300,394 | 11/1981 | Wiley . |
| 4,360,271 | 11/1982 | Downs et al. . |
| 4,372,163 | 2/1983 | Tittmann et al. . |

(List continued on next page.)

FOREIGN PATENT DOCUMENTS

| | | |
|---|---|---|
| 0262926A | 12/1985 | Japan . |
| 1227064 | 3/1971 | United Kingdom . |

OTHER PUBLICATIONS

P. Cielo, et al., "Laser Generation of Convergent Acoustic Waves and Applications to Materials Evaluatoin", IEEE 1986 Ultrasonics Symposium, pp. 515–526.

Brochure from Zygo Corp., "Mark IVxp Interferometer System", 1990.

McGraw–Hill Encyclopedia of Science & Technology, 1987 edition, vol. 9, pp. 289–297.

(List continued on next page.)

*Primary Examiner*—Frank Gonzalez
*Assistant Examiner*—Amanda Merlino
*Attorney, Agent, or Firm*—Perman & Green

[57] ABSTRACT

Disclosed herein is an interferometric-based materials analysis system (10) that employs a novel combination of laser beam shaping and pointing techniques, the use of a low cost, rugged, and compact diode laser (22) as a detection laser, and the use of signal processing techniques that compensate for inherent instabilities and short-term drift in the diode laser. A matched filter processing technique is disclosed for processing interferometrically-obtained data points from a target being analyzed. The matched filter technique is shown to be especially useful for detecting and analyzing Lamb modes within thin targets, such as a silicon wafer undergoing a rapid thermal processing cycle. Also disclosed is a method and apparatus for interferometrically monitoring a target to determine, in accordance with predetermined criteria, an occurrence of a period of time that is optimum for obtaining a data point. In response to detecting such a period an impulse source, such as an impulse laser (14), is triggered to launch an elastic wave within the target so that a data point can be obtained. A plurality of data points so obtained are subsequently processed, such as by the matched filter technique, to determine a property of interest of the target. The property of interest may be, by example, the temperature of the target or the metallurgical status of the target.

2 Claims, 18 Drawing Sheets

U.S. PATENT DOCUMENTS

| | | |
|---|---|---|
| 4,391,526 | 7/1983 | McLaughlin . |
| 4,468,551 | 8/1984 | Neiheisel . |
| 4,469,450 | 9/1984 | DiVincenzo . |
| 4,498,773 | 2/1985 | von Bieren . |
| 4,516,244 | 5/1985 | Holmes . |
| 4,521,118 | 6/1985 | Rosencwaig . |
| 4,522,510 | 6/1985 | Rosencwaig et al. . |
| 4,539,846 | 9/1985 | Grossman . |
| 4,541,279 | 9/1985 | Schomberg . |
| 4,541,280 | 9/1985 | Cielo et al. . |
| 4,541,720 | 9/1985 | Hausler et al. . |
| 4,545,248 | 10/1985 | Kitada et al. . |
| 4,598,408 | 7/1986 | O'Keefe . |
| 4,606,036 | 8/1986 | Holmes . |
| 4,622,202 | 11/1986 | Yamada et al. . |
| 4,633,715 | 1/1987 | Monchalin . |
| 4,636,088 | 1/1987 | Rosencwaig et al. . |
| 4,639,669 | 1/1987 | Howard et al. . |
| 4,655,608 | 4/1987 | Goss et al. . |
| 4,658,648 | 4/1987 | Roddeck et al. . |
| 4,659,224 | 4/1987 | Monchalin . |
| 4,688,940 | 8/1987 | Sommargren et al. . |
| 4,689,491 | 8/1987 | Lindow et al. . |
| 4,762,425 | 8/1988 | Shakkottai et al. . |
| 4,763,282 | 8/1988 | Rosenberg . |
| 4,854,710 | 8/1989 | Opsal et al. . |
| 4,890,921 | 1/1990 | Pond et al. . |
| 4,932,783 | 6/1990 | Kersey et al. . |
| 4,966,459 | 10/1990 | Monchalin . |
| 5,035,144 | 7/1991 | Aussel . |
| 5,052,661 | 10/1991 | Dunlay et al. ............................ 266/87 |
| 5,061,071 | 10/1991 | Fujita et al. . |
| 5,068,541 | 11/1991 | Kondo . |
| 5,080,491 | 1/1992 | Monchalin et al. . |
| 5,083,869 | 1/1992 | Nakata et al. . |
| 5,110,211 | 5/1992 | Niki et al. . |
| 5,131,748 | 7/1992 | Monchalin et al. . |
| 5,136,172 | 8/1992 | Nakata et al. . |
| 5,137,361 | 8/1992 | Heon et al. . |
| 5,286,313 | 2/1994 | Schultz et al. . |
| 5,317,748 | 5/1994 | Silva et al. . |
| 5,363,050 | 11/1994 | Guo et al. . |
| 5,373,741 | 12/1994 | Volkmann et al. . |
| 5,374,991 | 12/1994 | Atkinson et al. . |
| 5,383,366 | 1/1995 | Wallingford et al. . |
| 5,386,727 | 2/1995 | Searle . |

OTHER PUBLICATIONS

"Development and Evaluation of a Workpiece Temperature Analyzer for Industrial Furnaces" Energy Conservation, U.S. Dept. of Energy, May, 1990, pp. 1–61 plus Appendix A–1 –A–78.

"Development and Evaluationo f A Workpiece Temperature Analyzer For Industrial Furnaces" Energy Conservation, U.S. Dept. of Energy, Nov., 199, pp. 1–71.

L. Lynnworth et al., "New Sensors For Ultrasound: Measuring Temperature Profiles", Materials Research and Standards, vol. 10, no. 8 Aug. 1970, pp. 6–11 and 40.

H. Tasman et al., "The Ultrasonic Thermometer–Construction, Applicaiton, and Operating Experience", High Temperatures–High Pressures, 1972, vol. 4, No. 4, pp. 477–481.

"Polarization Interferometers for the Observation of Phase Objects", Chapter 4, Polarization Interferometers, pp. 45–54, (no date available).

A. J. denBoef, "Two–Wavelength Scanning Spot Interferometer Using Single–Frequency Diode Lasers", Applied Optics, vol. 27, No. 2, Jan. 15, 1988, pp. 306–311.

"Equal–Path, Phase Shiftin, Sample–Point Interfermoter", NASA Tech. Briefs, Apr., 1991.

Masanori Hangyo et al., "Photoacoustic Microscope", Dept. of Applied Physics, Faculty of Engineering Osaka University, vol. 36, no. 10, Oct. 1987, pp. 730–736.

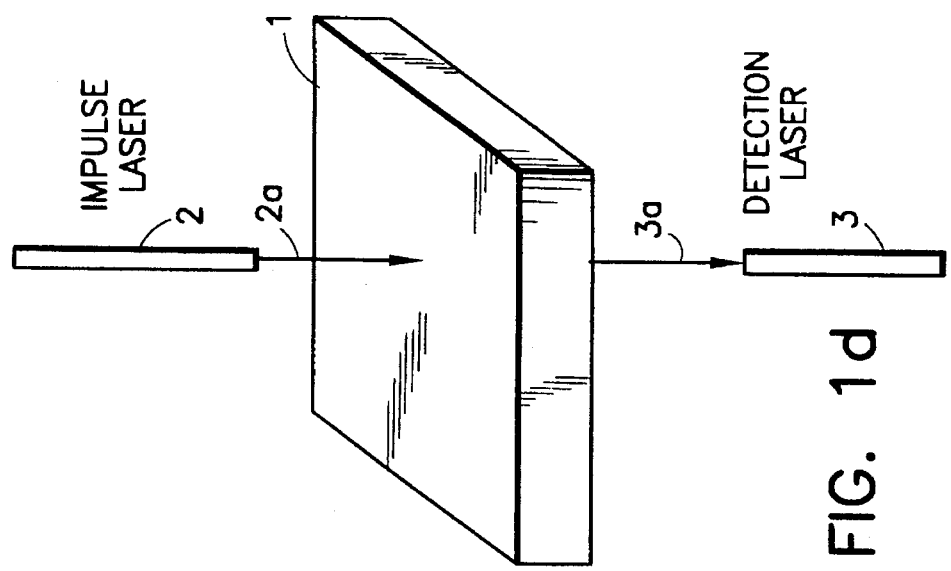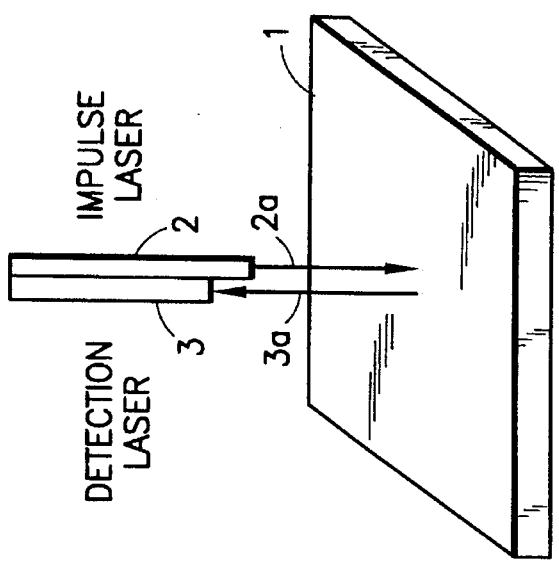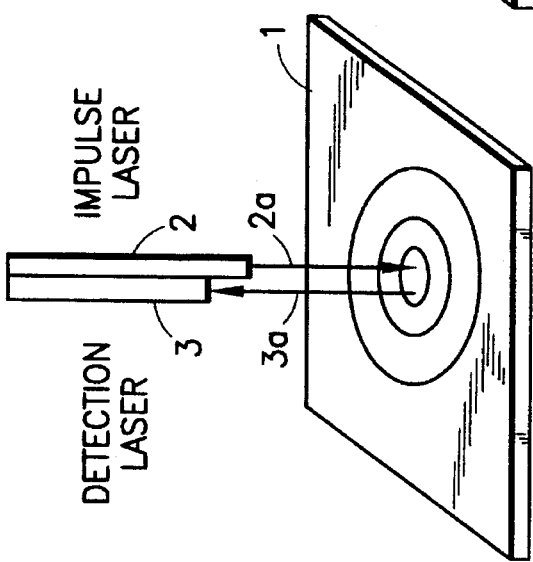

LASER ULTRASONICS-BASED MATERIAL ANALYSIS SYSTEM AND METHOD USING MATCHED FILTER PROCESSING

This is a divisional of copending application(s) Ser. No. 08/308,372 filed on Sep. 19, 1994 (still pending).

FIELD OF THE INVENTION

This invention relates generally to apparatus and method for remotely (non-contact) characterizing one or more properties of a target, such as the metallurgical status, structural integrity, dimensions, and/or temperature, through the use of ultrasonic energy that is induced within the target and the use of an optical system for detecting a corresponding motion of the surface of the target.

BACKGROUND OF THE INVENTION

The generation of elastic waves in a target is a well-characterized phenomenon. It is known that when transient changes in the structure of a target occur, elastic waves are generated both on the surface and in the bulk of the target. Referring to FIGS. 1a–1d, there are four types of waves which can propagate in a target, such as a solid 1, namely longitudinal, shear, Rayleigh or surface, and Lamb waves (shown in FIG. 10a). The longitudinal and/or shear waves travel only through the bulk of the solid, with the longitudinal waves having a velocity that is approximately twice that of the shear waves. The Rayleigh waves travel only on the surface of the solid with velocities slightly less than that of the shear waves. The Lamb waves are supported by and propagate through very thin solids, and may be used to measure the thickness of the solid 1. Longitudinal bulk waves and shear bulk waves have been extensively used for the detection of flaws, measurements of elastic properties of solids, and for the monitoring of phase transitions, such as occurs when a molten metal solidifies. It is also well-known to measure the temperature of the solid 1, as the temperature effects the velocity of the waves within the solid.

A number of different types of transducers have been employed to generate elastic or ultrasound wave energy in solids. Of most interest herein is the use of a laser (e.g., impulse laser 2) to generate ultrasound waves, coupled with the use of a detection laser 3, such as is found in an optical interferometer, to detect a movement of the surface of the solid 1 in response to the propagating ultrasound waves.

For example, by synchronizing the operation of the interferometer 3 with the Firing of the impulse laser 2, and by determining a difference between the impulse laser firing time and the time that the wave is detected, the velocity of the wave in the solid 1 can be determined; so long as the distance d is known between the spot where the impulse laser beam 2a impinges and where the detection laser beam 3a impinges. The determined velocity, or time of flight, may then be correlated with some property of interest of the solid, such as the structure of the solid or the temperature of the solid. For the case where the impulse laser beam 2a and the detection laser beam 3a are directed to opposite sides of the solid, as in FIG. 1d, it is possible to measure the thickness of the solid. The thickness can also be measured, with the impulse and detection laser beams impinging on the same side, if the solid is thin enough to support a Lamb wave.

A representative, but not exhaustive, list of U.S. Patents in this and related technical areas include the following: U.S. Pat. No. 3,601,490, issued Aug. 24, 1971 to K. Erickson and entitled "Laser Interferometer"; U.S. Pat. No. 3,694,088, issued Sep. 26, 1972 to J. Gallagher et al. and entitled "Wavefront Measurement"; and U.S. Pat. No. 4,633,715, issued Jan. 6, 1987 to J. Monchalin and entitled "Laser Heterodyne Interferometric Method and System for Measuring Ultrasonic Displacements". Also of interest is U.S. Pat. No. 5,286,313, issued Feb. 15, 1994 to Thomas J. Schultz, Petros A. Kotidis (an inventor of the subject matter of this patent application), Jaime A. Woodroffe (an inventor of the subject matter of this patent application), and Peter S. Rostler. The subject matter of this U.S. Patent, entitled "Process Control System Using Polarizing Interferometer", is incorporated by reference herein. The preferred embodiment of the system described in this patent employs an XeCl impulse laser in combination with a Helium-Neon-based polarizing interferometer to provide, by example, remote detection of a temperature of a workpiece.

One intended operating environment for this type of system is in a metals fabrication and/or treating facility. As can be appreciated, and because of the ambient heat, vibration and airborne particulate matter that is typically found in this type of environment, severe demands and operating stresses are placed on the interferometer and its associated detection laser and optical elements.

Another important consideration is the cost of the system, as an industrial application may require the use of a number of materials analysis systems. That is, it is desirable to provide a rugged, compact and low cost system without compromising measurement accuracy and repeatability.

Although the system described in U.S. Pat. No. 5,286,313 is well-suited for use in its intended application, it is an object of this invention to provide an improved laser ultrasonics materials characterization and analysis system.

SUMMARY OF THE INVENTION

This invention provides an interferometric-based laser ultrasonics materials analysis system that is improved over known types of systems. This is achieved through a novel combination of laser beam shaping and pointing techniques, the use of a low cost, rugged, and compact diode laser assembly as a detection laser, various techniques to optimize the system for use with the diode laser-based detection laser, and the use of signal processing techniques that compensate for inherent instabilities and short-term drift in the diode laser. In addition, matched filter processing techniques are disclosed for processing interferometrically-obtained data points from a target being analyzed.

Also disclosed is a method and apparatus for interferometrically monitoring a target to determine, in accordance with predetermined criterion, the occurrence of a period of time that is optimum for obtaining a data point. In response to detecting such a period an impulse source, such as an impulse laser, is triggered to launch an acoustic wave within the target so that a data point can be obtained. A plurality of data points so obtained are subsequently processed, such as by the matched filter technique, to determine a property of interest of the target. The property of interest may be, by example, the temperature of the target or the metallurgical status of the target.

BRIEF DESCRIPTION OF THE DRAWINGS

The above set forth and other features of the invention are made more apparent in the ensuing Detailed Description of the Invention when read in conjunction with the attached Drawings, wherein:

FIGS. 1a–1d generally illustrate various types of waves that may be supported within a solid and various configurations of impulse and detection lasers for generating and detecting these waves;

FIG. 13a is a top view of a furnace showing the system of this invention being used to examine boiler tubes for hot spots; while FIG. 13b is a detail of one of the boiler tubes.

DETAILED DESCRIPTION OF THE INVENTION

Figure 2:
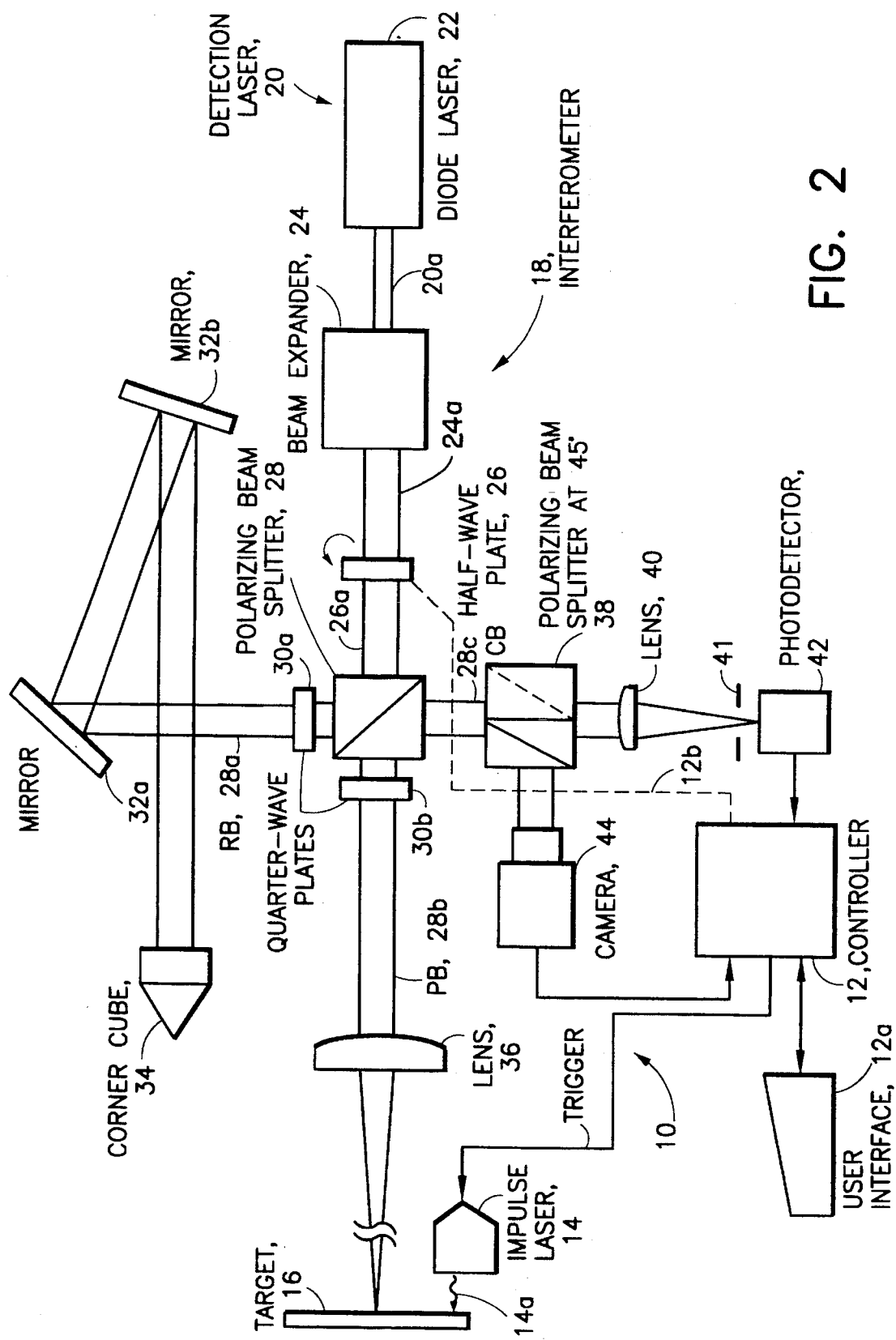
FIG. 2 is a block diagram of a laser ultrasonics materials analysis system in accordance with this invention.

FIG. 2 is a block diagram of a presently preferred embodiment of a laser ultrasonics materials analysis system 10 that is constructed and operated in accordance with this invention. The system 10 generally operates by launching an elastic wave within a target, sensing a surface displacement of the target due to the elastic wave, and then correlating the sensed displacement with a value of a property or properties of interest. As employed herein an elastic wave is intended to also encompass an acoustic wave. Also as employed herein a target may be a solid, a semi-solid, or a liquid.

A system controller 12, such as an embedded microprocessor or an externally connected computer or workstation, includes a user interface 12a that includes, by example, a touchscreen and/or a conventional keyboard and/or a pointing device (e.g., mouse) in combination with a graphical display device through which a user is enabled to interact and direct the operation of the system 10. An impulse laser 14 is controlled by the controller 12 to provide an impulse beam 14a to the surface of an object, hereafter referred to as a target 16 (the target forms no part of the system 10, and is shown only for completeness). The impulse beam 14a causes a localized heating of the target 16 and launches an elastic wave within the target as described previously. A displacement of the surface of the target 16 due to the elastic wave is detected by a polarizing interferometer 18 that is constructed and operated in accordance with this invention.

The interferometer 18 includes a detection laser 20 which, in the presently preferred embodiment of the polarizing interferometer 18, includes a diode laser 22. The diode laser 22, provides high power (>100 mW) along with the combined characteristics of small dimensions, low cost (relative to more conventional detection lasers such as the He—Ne), and a long coherence length (i.e., narrow bandwidth). Commercially available diode laser systems can provide >100 mW of power with bandwidths that range from 10 MHz to less than 10 KHz. The selection of a particular diode laser for use in the system 10 is a function of the required power, coherence length, wavelength, system compactness, and cost. Included with the detection laser 20 is a conventional Faraday rotator (not shown) to prevent any reflected laser light that returns from the target 16 from effecting the performance of the diode laser 22. Although the operating characteristics of the interferometer 18 ensure that the returned laser light intensity is very small, even a small amount of returned laser light can adversely effect the wavelength characteristics of the laser diode 22. The output of the detection laser 20 assembly is a source beam 20a.

Figure 16:
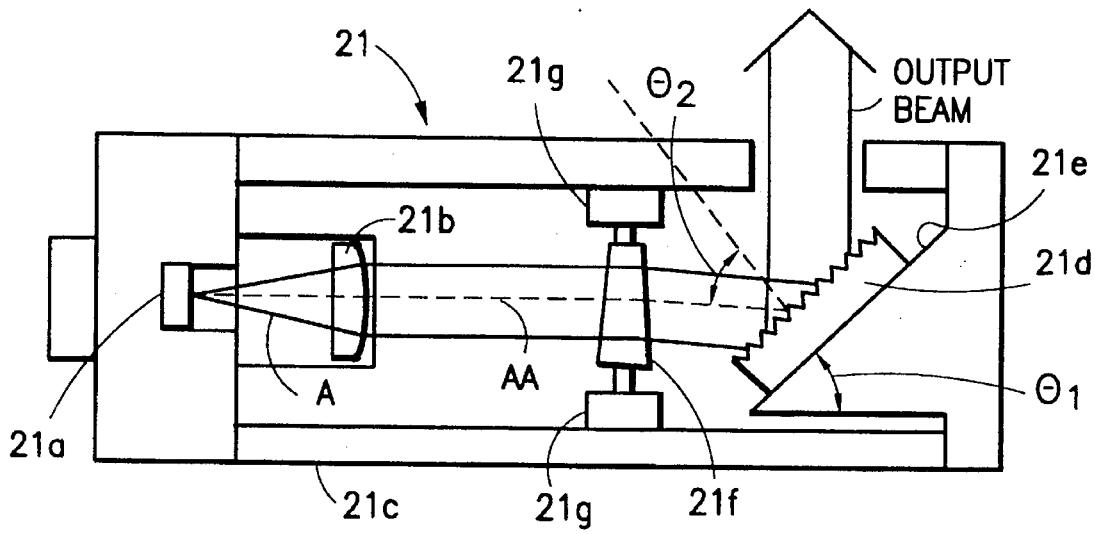
FIG. 16 is a simplified cross-sectional view of a laser diode assembly in accordance with an aspect of this invention.

Reference is now made to FIG. 16 for illustrating a novel and preferred diode laser assembly 21. It is first pointed out that some diode lasers have been conventionally stabilized by an external cavity formed by a grating mounted in a Litetrow configuration. The first order reflection off the grating provides feedback into the laser cavity and the zero order reflection provides the output coupling.

The diode laser assembly 21 of FIG. 16 employs a novel technique for mounting and aligning a grating which is very stable (thermally and mechanically), and at the same time inexpensive to manufacture and simple to construct.

A laser diode 21a outputs a beam designated as 'A'. The laser diode 21a and a collimating lens 21b are mounted on an end of a support structure (e.g., a tube 21c made from stainless steel or some other suitable rigid material). By example, the tube 21c has a length of six inches and a diameter of two inches. The diode laser 21a has an anti-reflection (AR) coating on its output facet to eliminate facet modes which would conflict with external modes established by a grating 21d. The grating 21d is mounted on a fixed angle pedestal 21e, the angle (81) of which is selected to provide a desired operating wavelength of the laser diode 21a. By example, if a 1800 groove per millimeter grating is used, the accuracy of the machined angle required for tuning the laser diode emission to ±1 nm is approximately ±0.8 degrees, a value well within simple machining tolerances.

Since the tuning range of the diode laser 21a is large (10's of nm) the angle of the tuning axis (in the plane of the drawing) is not critical and, thus, no adjustment mechanism is necessary (although one may be provided if desired). However, the angle out of plane (the alignment axis AA) cannot be readily machined to sufficient accuracy. As a result, this angle is adjusted by rotating a wedge 21f about the axis approximately parallel to the laser beam. The wedge 21f is positioned between the diode laser 21a and the grating 21d and functions to change the angle of the laser beam. The wedge 21f is supported by a rotation stage mount 21g. In FIG. 16 the angle $\theta_2$ is the Littrow angle associated with the grating 21d, and the optical cavity external to the diode laser 21a extends generally to the face of the grating 21d.

If the wedge 21f is initially rotated so that the deflection produced is in the same plane as the incidence plane on the grating 21d, then small rotation angle changes of the wedge 21f will have very little impact on the tuning angle, while allowing sufficient control on the alignment axis angle. As an example, if a 10 degree quartz wedge is used, a 10 degree rotation of the wedge 21f will result in a 0.8 degree change in the alignment axis, with only a 0.9 nm change in the tuned wavelength.

The wedge 21f is preferably anti-reflection coated to minimize cavity losses, and is also tilted with respect to the beam axis so that reflections off either wedge surface will not go back into the laser diode 21a.

Referring again to FIG. 2, the source beam 20a is provided to a beam expander 24. The characteristics of the beam expander 24 directly impact the light collecting power of the sensor system described below. In general, the larger the beam diameter, the larger the return speckle size, and thus the greater is the fraction of the total returned power that is available to interference signal generation.

The beam expander 24 can be placed either before or after a polarizing beam splitter 28 that is described below. Placing the beam expander 24, after the beam splitter 28 has the advantage that the interferometer optics can be made smaller and also independent of the expansion ratio of the beam expander 24. However, placing the beam expander 24 at this position requires that the detection or probe beam (PB) 28b pass through the beam expander 24 twice. As a result, the quality (cost) and alignment of the beam expander 24 becomes important to the overall operation of the system 10. As such, and although it is preferred to place the beam expander 24 before the polarizing beam splitter 28, as illustrated in FIG. 2, the teaching of this invention is not so limited.

The expanded source beam 24a next encounters a halfwave plate 26 that is located before the polarizing beam splitter 28. The halfwave plate 26 provides a mechanism for setting a desired ratio for a reference beam (RB 28a) to probe beam (PB 28b) intensity. Varying the rotation angle of the halfwave plate 26 rotates the polarization of the laser beam and, in combination with the operation of the polarizing beam splitter 28 that is described next, thereby controls the fraction of the beam going into the PB 28b and into the RB 28a of the interferometer 18.

In accordance with an aspect of this invention the halfwave plate 26 may be coupled to a mechanism, such as a motor, for imparting a rotary motion to the halfwave plate 26. In this embodiment the controller 12 automatically monitors the signal returned from the target 16 and controllably rotates the halfwave plate 26, via signal line 12b, so as to optimize the relative intensities of the reference and probe beams. Alternately, this function can be performed by a user who monitors a graphical display provided by a camera 44 (described below).

The rotated beam 26a that passes through the halfwave plate 26 is split into the RB 28a and PB 28b by the polarizing beam splitter 28, with the RB 28a and PB 28b having relative intensities set by the rotation imparted by the halfwave plate 26. After the reference and probe beams 28a and 28b leave the polarizing beam splitter 28 each passes through an associated ¼ wave retardation plate 30a and 30b, respectively. Plates 30a and 30b are aligned so that both of the RB 28a and PB 28b are circularly polarized.

The path length of the RB 28a is adjusted to reduce the noise in the signal that is detected from a combined beam (CB) 28c. The degree to which the lengths of the probe leg and the reference leg are matched is a function of the bandwidth of the diode laser 22, the fraction of the signal noise that is attributed to any frequency jitter of the diode laser 22, and the impact of the length of the reference leg on the overall compactness of the interferometer 18.

Included within the RB 28a leg are a plurality of folding mirrors 32a and 32b and a corner cube reflector 34. It is important to the operation of the interferometer 18 that the reference leg return beam be at the same angle (opposite direction) as the outgoing reference beam. This important goal is achieved in a simple, compact, and inexpensive manner using the corner cube 34. In contrast, a simple mirror would require careful and precise adjustment, and very high quality mounts all along the reference path to maintain the alignment. In the presently preferred embodiment of this invention these requirements are eliminated by the use of the corner cube 34 (preferably gold coated and hollow) which terminates the reference beam path leg while preserving the polarization characteristics of the RB 28a.

The PB 28b is focussed to a point on the target 16 using a lens 36 that has a focal length equal to the distance to the target 16. That portion of the PB 28b that reflects from the surface of the target 16 is subsequently collimated by the lens 36 as it travels back into the interferometer 18.

The same prism (the polarizing beam splitter 28) that is used to split the polarized beam 26a into the RB 28a and the PB 28b is also is used to recombine the RB 28a and the returned (reflected) portion of the PB 28b into a combined beam (CB) 28c. Because the RB 28a and the PB 28b are circularly polarized, and just pass back through the ¼ wave plates 30a and 30b, respectively, they are again linearly polarized, but at the opposite orientation than their original linear polarizations. Because of this, the CB 28c does not go back toward the diode laser 22, but instead is directed into a signal detection portion of the interferometer 18.

Figure 5:
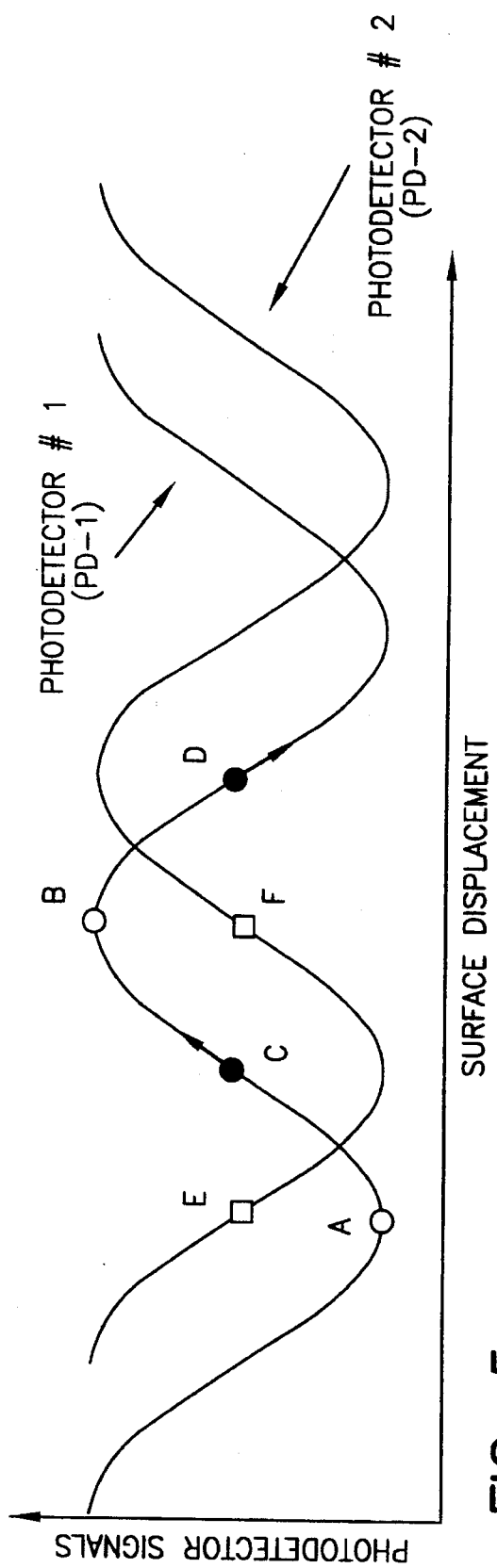
FIG. 5 illustrates a transfer function of a polarizing interferometer that uses two detectors 90° out of phase.

As was stated, after the RB 28a and the PB 28b are combined they are both linearly polarized, but of the opposite sense. In order to generate an interference signal (detectable interference fringes), a polarizing prism or beam splitter 38 oriented at 45° is used to select a projection of the polarization axis of each of the RB 28a and the PB 28b along a common axis. This results in two combined beams whose interference signal is 180° out of phase. Either or both of these beams can be used to provide the signal necessary for process analysis. For example, FIG. 5 illustrates the use of two photodetectors (PD-1 and PD-2) for detecting two combined beams. A combined beam focussing lens 40 is used to focus the CB(s) 28c onto a radiation sensitive surface of one or more photodetectors 42. The lens 38, in combination with an aperture 41, can also be used to spatially block out light other than that of the combined beams from impinging on the photodetector 42.

The photodetector 42 may be provided in a number of suitable forms, depending on performance characteristics. Both conventional photomultiplier tubes and hybrid photodiode/amplifiers are suitable embodiments for detecting the light and dark pattern that results from the interference of the RB 28a and the returned portion of the PB 28b within the CB 28c. The output of the detector 42 is provided to the controller 12 for signal processing in the manner described below.

An optional camera 44 is primarily used as a diagnostic tool, i.e., the camera 44 useful for optimizing the detected signal when an operator is setting up and controlling the system 10. For example the camera 44, which may be a conventional CCD device that provides an output to a display monitor of the user interface 12a, provides visual feedback to the operator for best signal return, which implies a best pointing angle to the target 16. However, in one embodiment of the invention an automatic beam steering system performs this function without operator intervention. The camera 44 may also be used for alignment of the signal and reference beams. The camera 44 can also be employed to determine the relative intensity of the reference and signal beams and, based on the indicated intensities, the operator is enabled to rotate the halfwave plate 26 to achieve an optimum intensity distribution for optimum fringe contrast.

It should be realized that if the camera 44 is eliminated a second photodiode 42 can be installed in its place. The use of a second photodiode 42 enables a square and add signal processing technique to be used as described in U.S. Pat. No. 5,286,313, which has been incorporated by reference herein.

Figure 3:
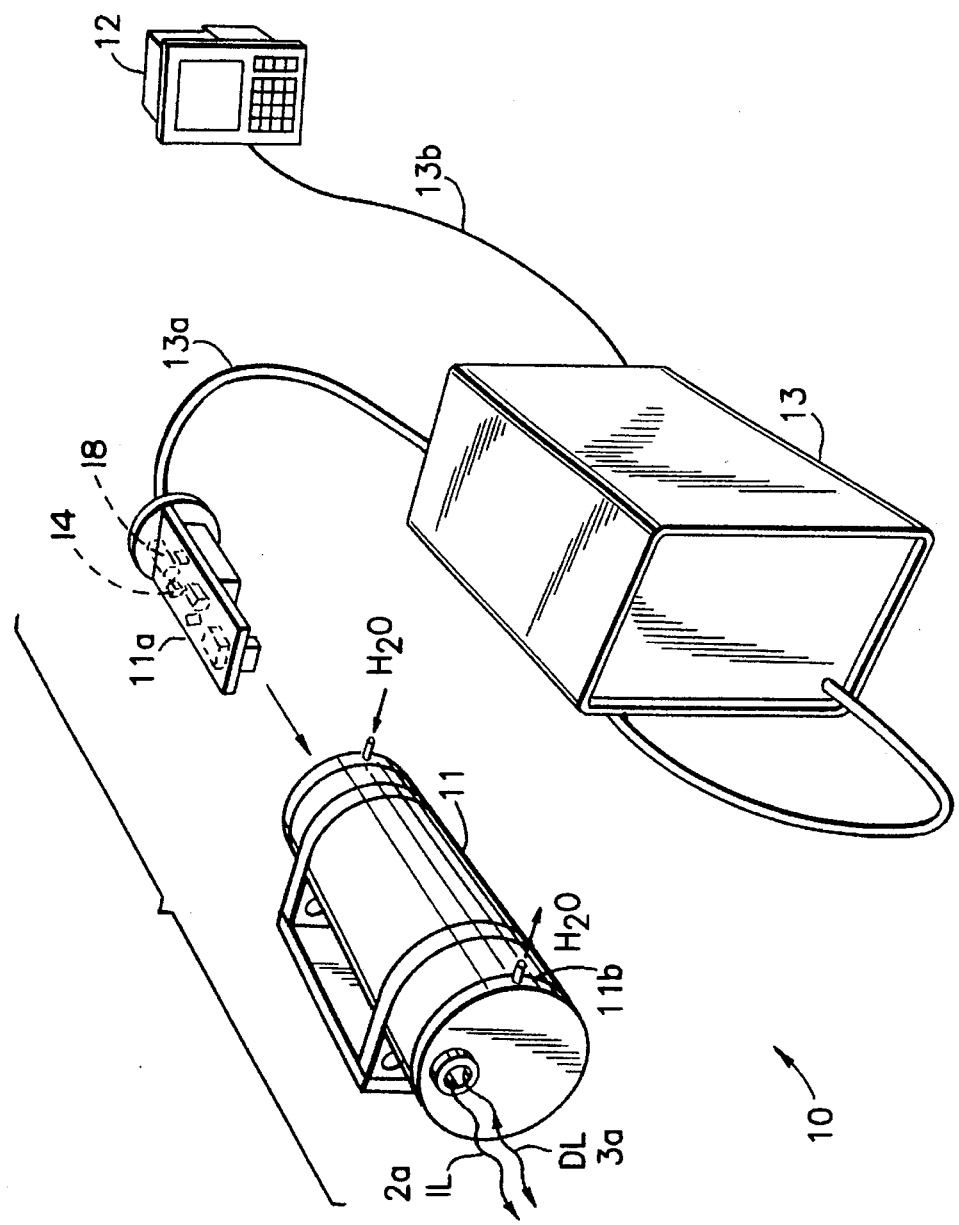
FIG. 3 is an elevational view of one embodiment of a laser ultrasonics system constructed in accordance with this invention.

FIG. 3 depicts an elevational view of the system 10, and shows a bulkhead-mounted optical head 11, a base unit 13, and the controller 12. The optical head 11 is constructed to have a slide-in unit 11a that contains the impulse laser 14, the interferometer 18, and all associated electronics and controls. Preferably, the optical head 11 includes a jacket 11b through which a cooling fluid (e.g., water) is flowed during the operation of the system 10. The slide-in unit 11a is thermally coupled to the water jacket 11b when inserted into the head 11, which thereby functions to remove the heat that is generated by the operation of the lasers and associated electronics, although a primary function of the water jacket 11b is to remove the external heat load during high temperature operation. The base unit 13 contains all required power supplies and provides, via cabling 13a and 13b, an interface to the controller 12. In a further (unillustrated) embodiment of the invention the optical head is instead tripod-mounted and may not be water-cooled.

Figure 4:
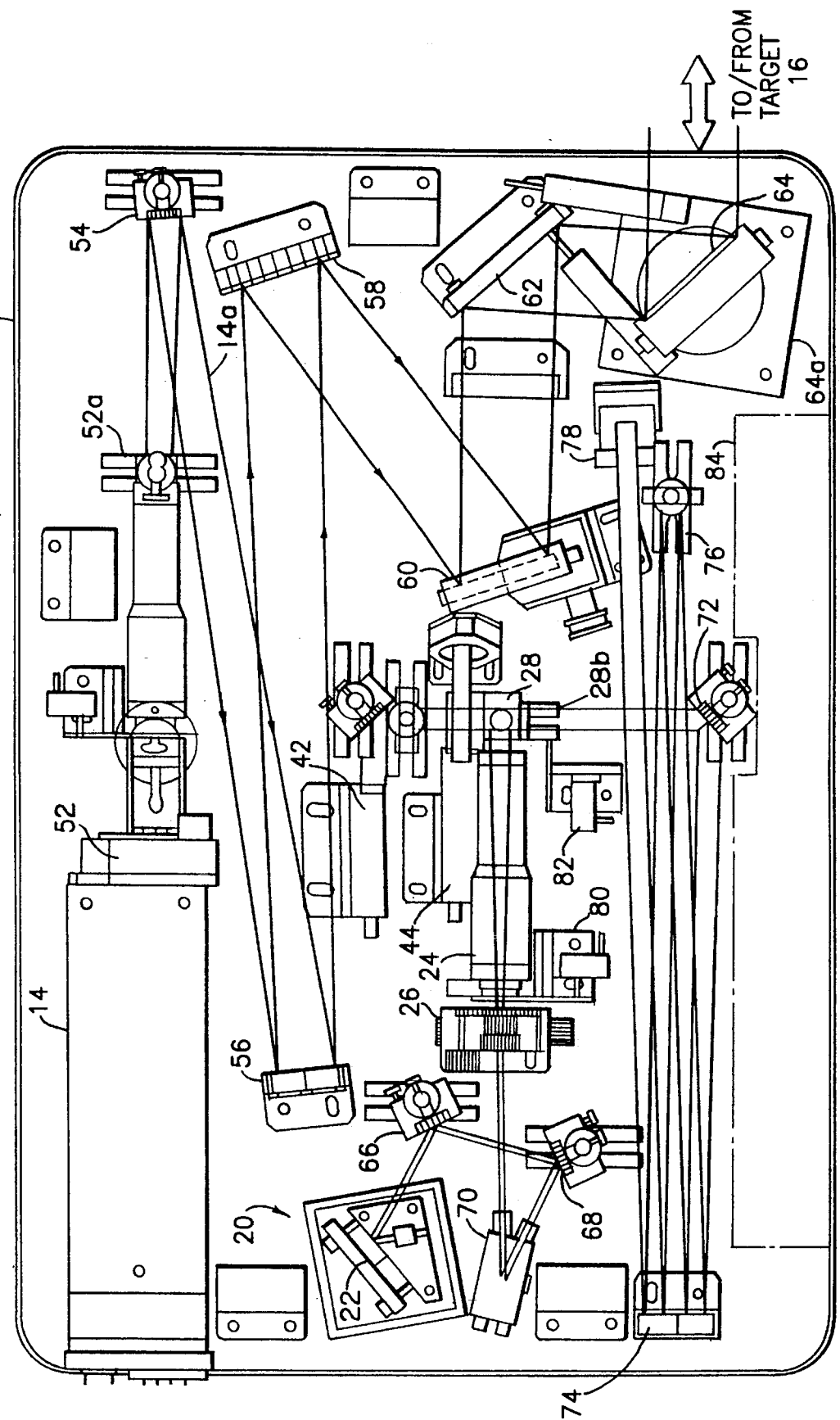
FIG. 4 is top view that illustrates a component placement and layout of an optical head portion of a system embodiment that is similar to that of FIG. 3.
Figure 7A:
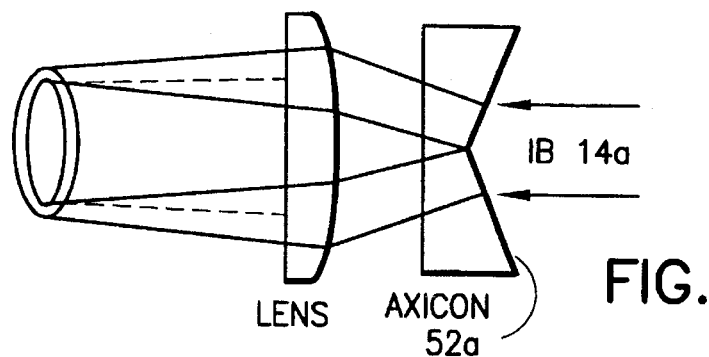
FIG. 7a is a cross-sectional view of an axicon used for impulse laser beam shaping in accordance with a first embodiment of this invention.

FIG. 4 is a top view of an exemplary embodiment of a slide-in unit 11a that is suitable for use in the above-mentioned tripod-mounted embodiment of the invention. A baseplate 50 provides a rigid support for mounting all of the required lasers and optical components. The impulse laser 14 has its output connected to a variable beam attenuator 50 and to a beam-shaping negative axicon 52a (FIG. 7a). The negative axicon 52a provides, in accordance with an aspect of this invention, a ring-shaped annular impulse beam 14a for impinging on the target 16. In another embodiment of the invention a waxicon 52b (FIGS. 7b and 7b') is employed instead. One difference between these embodiments is that the negative axicon 52a works in transmission, while the waxicon 52b works in reflection. A second difference is that the use of the waxicon shortens the beam path.

The shaped impulse beam is folded by mirrors 54, 56, 58 and combiner 60 before being provided to rotatably mounted beam steering mirrors 62 and 64, connected to a motor 64a, which direct the impulse beam 14a towards the target 16 at a controlled and optimum angle. This aspect of the invention is described in detail below with regard to FIGS. 8a and 8b.

The detection laser 20 is provided as a modular unit that includes the laser diode 22 and an externally mounted resonant cavity for narrowing the bandwidth of the laser diode 22. It is also preferred to use an antireflection (AR) coating to eliminate any internal modes of the laser diode. It is further preferred to employ a current control technique that uses a photodiode detector to sense any instability in the output of the laser diode 22 and, in response, that perturbs the laser diode current by some predetermined amount (e.g., 0.1%–1%). The laser diode 22 is operated as a continuous duty device. That is, and as will be made apparent below, an interference signal from the target 16 is available whether or not the impulse laser 14 is being triggered. A preferred embodiment of a diode laser assembly is illustrated in FIG. 16 and was described previously.

The output of the laser diode 22 is provided via mirrors 66 and 68 to the aforementioned Faraday rotator 70 and then to the halfwave plate 26 (beam polarization rotator). In this embodiment of the invention the beam polarization rotator 26 is positioned in front of the beam expander telescope 24. Coupled to the output of the beam expander telescope 24 is the polarizing beam splitter 28. The output of the beam splitter 28 impinges on a mirror 72 from which it is directed to an optical path wherein the beam is folded a number of times between a mirror 74 and reflectors 76 and 78. The probe beam 28b is output along with the impulse beam 14a towards the target 16 via the beam steering mirrors 62 and 64.

The folding of the probe beam between mirrors 74, 76 and 78 is an aspect of this invention related to the use of the diode laser as the detection laser 20. The coherence length of a typical diode laser is in the range of 30 meters to 40 meters. For an unequal path length interferometer (wherein a difference between the probe beam path length and the reference beam path length is large), this would imply that suitable interferometric detection would occur. However, there still may be sufficient frequency jitter to contaminate the measurement of small displacements of interest. This is overcome in the system 10 by path matching the probe beam path to the reference beam path with the mirrors 74, 76 and 78 to provide an equal or approximately equal path length interferometer and a significant increase in the SNR. This path matching is used in combination with the grating 21d (FIG. 16), the Faraday rotator, the beam expanding telescope 24, and the focussing lens 36 (to provide at least one bright speckle), in order to optimize the interferometer 18 for use with a diode laser as the detection laser.

Referring again to FIG. 4 the components 80 and 82 are shutters. Also shown is the camera 44, the photodetector 42 and, in dashed outline 84, a support electronics package. As can be appreciated, the impulse laser system and the interferometer 18 are provided in a small area and the beams are tightly folded to minimize the required mounting area.

It is within the scope of the invention to provide the impulse beam 14a with a shape that corresponds to a ring, a line, or a point. The ring-shape is preferred (using the negative axicon 52a or the waxicon 52b), but there are many applications where the other shapes become important. The probe beam 28b is preferably tightly focussed to a diffraction limited spot. For the annular ring-shape of the impulse beam 14a the probe beam 28b is located at the center of the ring (FIG. 7c), and the time of flight (TOF) of the elastic wave launched by the IB 14a is measured across the radius of the ring. For the line and point impulse beam shapes the probe beam 28b is separated by a fixed distance d, for example 0.5" to 1", away from the impulse beam 14a (see FIGS. 7d and 7e, respectively), and the TOF is measured across the distance d.

An important aspect of the design of the negative axicon 52a used in this invention is that the conical surface is concave. The same impulse laser ring-shape on the target can be obtained with a convex surface (positive) axicon, but immediately after the axicon there will be a caustic focus which creates a line-shaped zone of intense laser fluence which can cause damage to optics placed in its path. The length of this zone extending from the axicon is a function of the angle of the axicon and the diameter of the impulse beam, and can extend several inches. With the concave surface axicon there is no limit on how close subsequent optics can be placed. As such, the use of the concave surface axicon is preferred, although the teaching of this invention is not limited to only this configuration.

A problem that arises during the use of an axicon is that the impulse beam 14a ring diverges and the diameter of the ring on the target will vary as a function of distance to the target. Such a situation is unacceptable as the system 10 would not operate correctly with moving or vibrating targets because the target distance, and thus the diameter of the IB 14a ring, will change continuously. In this case the time of arrival of the elastic waves at the location of the PB 28b will also be continually changing, and there would be no way to distinguish between a change in the arrival time due to the target motion (a change in ring diameter) or that due to a change in a property of the target (a change in elastic wave arrival time).

This problem is overcome in the system 10 by ensuring that the ring-shaped IB 14a exiting the head 11 is of constant diameter and is not expanding (diverging) or converging. This is achieved by causing the impulse beam 14a to travel a predetermined distance within the head 11 before it is focused onto the target 16. The predetermined distance is approximately equal to the distance of the head 11 to the target 16, and is achieved through the use of adjustable path length folding optics represented by the components 54, 56, 58, 60 and 62 of FIG. 4.

Figure 7B:
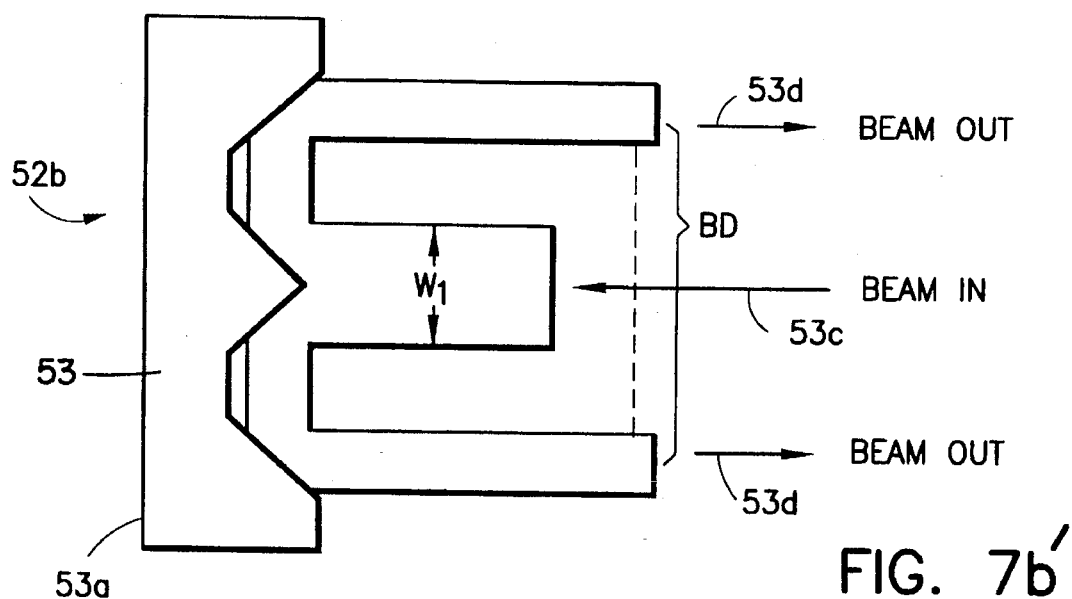
FIGS. 7b and 7b' are each a cross-sectional view of a waxicon used for impulse laser beam shaping in accordance with a second embodiment of this invention.
Figure 7B:
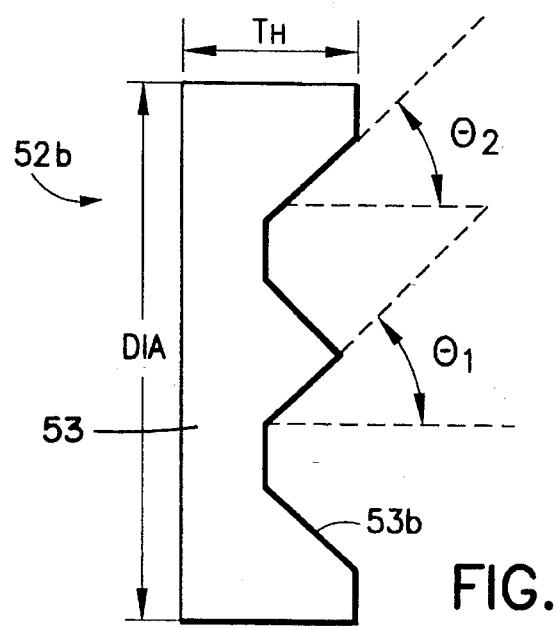
Figure 7C:
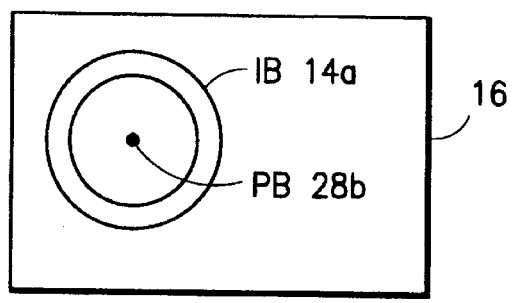
FIGS. 7c–7e illustrate various impulse beam shapes, and their relationship to a probe beam, in accordance with the invention.
Figure 7D:
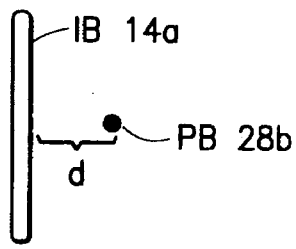
Figure 7E:
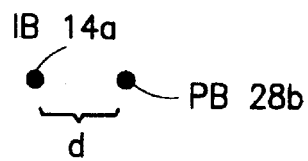

The optical properties of the reflective waxicon 52b of FIGS. 7b and 7b' also solve this problem of impulse beam divergence or convergence and provide an impulse beam ring of constant diameter, while reducing or eliminating the requirement to provide the extended light path inside the head 11. As a result, the use of the waxicon 52b is desirable to reduce the volume of the head 11.

Referring now to FIGS. 7b and 7b' there is illustrated one suitable embodiment of the waxicon 52b. The waxicon 52b is comprised of a substrate 53, such as aluminum, having a diamond machined reflective surface 53b ($\lambda/4$). A suitable diameter is three inches, and a suitable maximum thickness (TH) is one inch. A suitable value for angle $\theta_1$ is 45°, while a suitable value for angle $\theta_2$ is approximately 45.3°. In response to an input beam 53c having a diameter of approximately 18 mm an annular output beam 53d is generated with a diameter (BD) of approximately two inches. Other materials, dimensions and angles may be employed, depending on the requirements of a particular application.

As has been previously indicated, the impulse beam 14a and the probe beam 28b may be located on the same side of the target 16 or, with additional reflectors and path optics, on opposite sides of the target 16.

The stability of the probe beam 28b is determined by the duration of a time interval during which the wavelength of the detection laser 20 can shift by no more than a predetermined maximum quantity or number of wave numbers. In the preferred embodiment of the invention the maximum quantity or number of wave numbers corresponds to a frequency in the range of 10 kHz to 100 kHz. However, this stability requirement is at or beyond the limit of the capabilities of currently available laser diode systems, or of most if not all types of laser systems that would be required to operate in the adverse environments within which the system 10 may be required to operate.

What makes the measurement of the minuscule target surface displacements possible is the fact that the detection beam is required to be stable for only a short period of time, e.g., 10 μsec at most, which corresponds to the time required to fire the impulse laser 14 and obtain a reading from the photodetector 42. In other words, this short term stability feature would be of little or no interest to a conventional user of diode lasers, but is exploited to its maximum potential in the system 10 in this invention.

In order to accommodate the different wavelengths of the diode laser 22 and the impulse laser 14, and still maintain the compactness of the head 11, a combination of mirrors 62 and 64 is employed to steer both beams (it being remembered that the impulse beam 14a may be a ring with the PB 28b at its center).

Figure 8A:
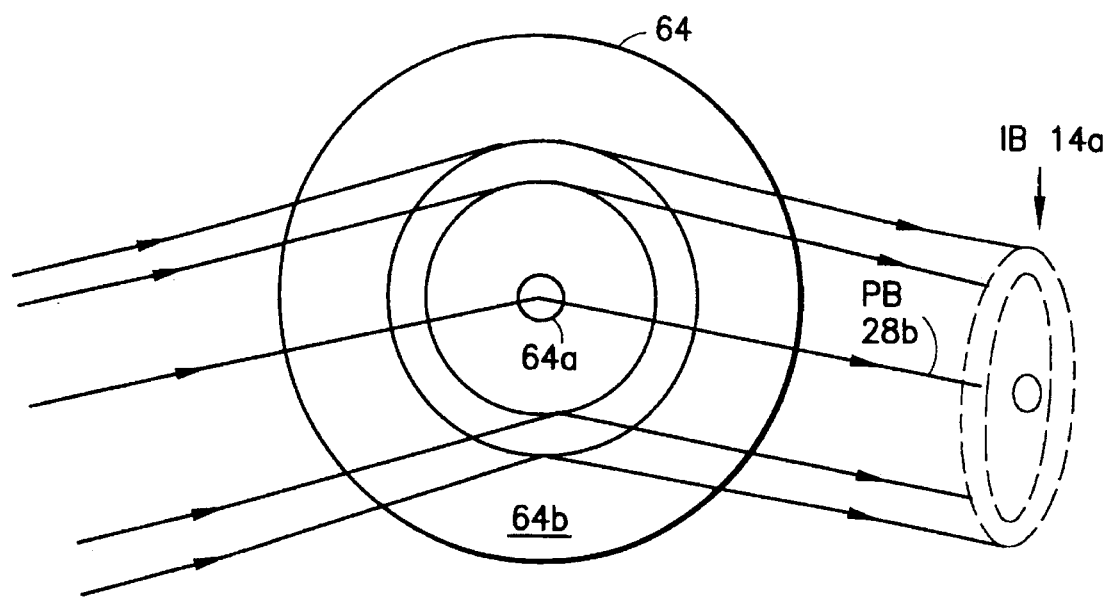
FIG. 8a is a front-facing view of a presently preferred embodiment of a beam-steering mirror that is used for directing an annular impulse beam and a spot probe beam in accordance with an embodiment of this invention.

As is shown in FIG. 8a, preferably the beam steering mirrors (actually the combination of the mirrors 62 and 64) have a reflective "patch" in their center, i.e., a small area 64a that is coated with a metal (e.g., gold) to reflect the PB 28b (which is in the infrared spectrum), while the remainder of the surface of the mirror 64 has a conventional dielectric coating 64b to reflect the impulse beam 14a, which may be in the green portion of the visible spectrum. Since the energy flux of the impulse beam 14a is quite high, providing a dielectric coating is desirable to avoid optical damage. In addition, the PB 28b must maintain its polarization during reflections, and hence the metallic (gold) patch 64a is preferred over a conventional dielectric-coated mirror, which will induce a change in polarization. The use of specific reflection materials and dielectric coatings can be generalized to whatever combination is appropriate for the wavelengths that are being used.

In this regard the choice of the IB 14a and the PB 28b wavelengths is not random, and there are several criterion involved in a specific choice of wavelengths. For example, the laser light interaction with the target surface is wavelength-dependent, and it has been found that metal targets respond best to green or ultraviolet (UV) wavelengths for the IB 14a. However, many composite materials give optimum results with IB 14a wavelengths in the far infrared. In addition, the sensitivity of the photodetector 42 is a function of the wavelength of the CB 28c and, hence, the emission wavelength of the laser diode 22.

While the system 10 is observing a target with a very diffuse reflectivity (near Lambertian), it is not critical that the viewing axis is normal to the surface. In fact, the intensity is still 50% of its peak value when the viewing axis is 45 degrees off normal. There are, however, surfaces such as those associated with non-polished metallic materials where the intensity drops of much faster as a function of angle. The intensity may drop to 10% of its peak value in a range of 1 to 10 degrees. For these situations it is desirable to provide an automatic system which adjusts the beam angle (preferably both impulse and probe) to stay near normal to the surface. This is important for applications such as viewing a moving strip in a metals processing plant where a common twisting motion of the strip can change the angle by as much as ±10 degrees.

Figure 8B:
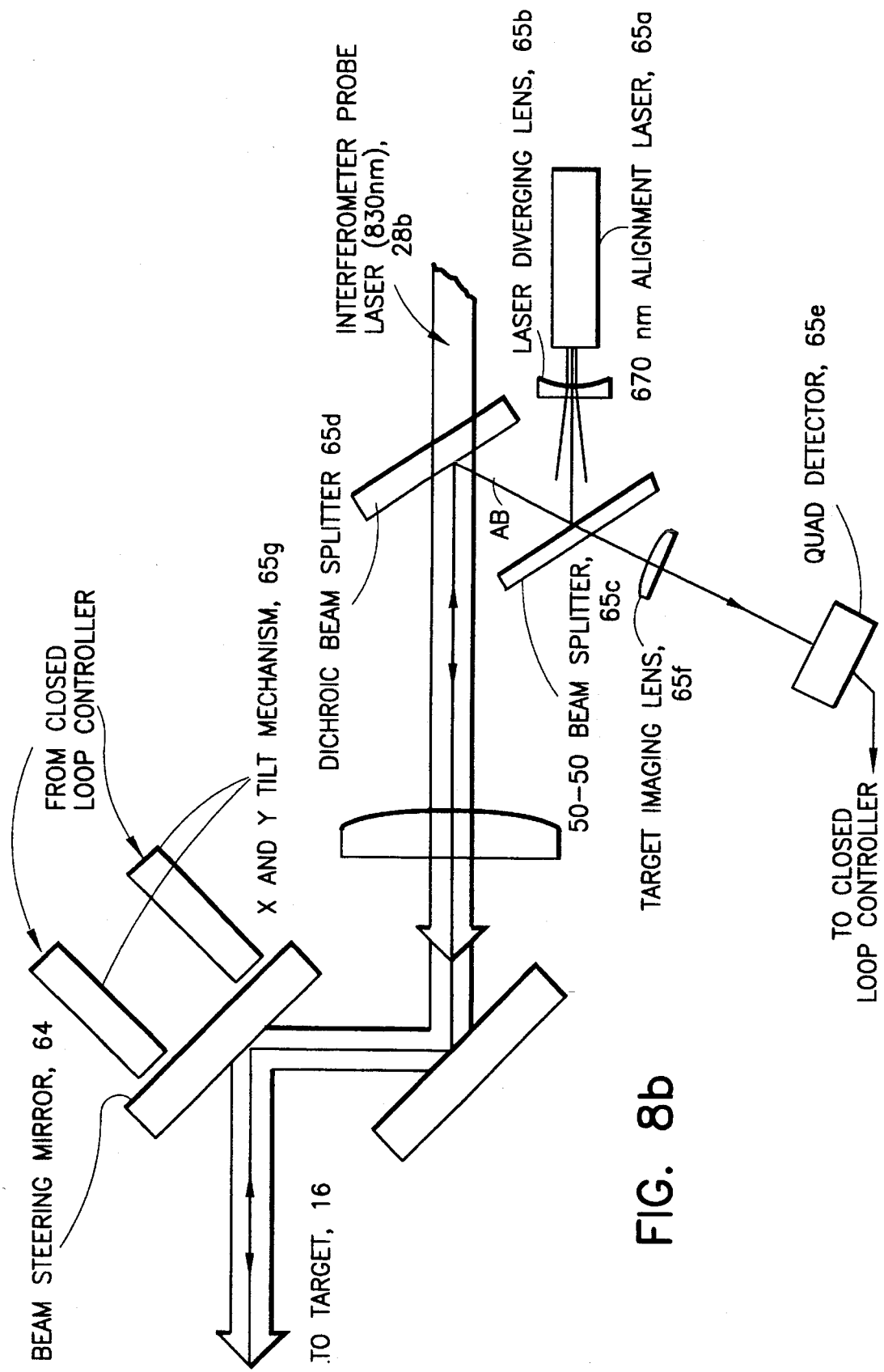
FIG. 8b is a block diagram of an automatic beam steering system in accordance with an aspect of this invention.

Referring to FIG. 8b this is accomplished by providing an alignment laser 65a, such as a diode laser operating at 670 nm (i.e. different wavelength from the wavelength (e.g., 830 nm) of the interferometer probe laser 20). The output of the alignment laser 65a passes through a lens 65b which is selected so that the beam coming out of the instrument illuminates a spot on the target which, relative to the position of the instrument window, subtends an angle larger than the possible angular variation of the target 16. The alignment beam from alignment laser 65a is combined with the PB 28b from detection laser 22 using a dichroic beam splitter 65d. The dichroic beam splitter 65d reflects the alignment laser beam AB but transmits the PB 28b. Alignment laser light returning from the target 16 is imaged onto a position sensitive detector 65e with an imaging lens 65f. One suitable embodiment for the detector 65e is a well known silicon quadrature detector. The imaging lens 65f is selected to have the beam spot on the target imaged to about the same size as the detector 65e. A 50/50 beam splitter 65c provides a simple method to both reflect out the alignment laser, and pass the returning beam (returning on the same axis AB) to the imaging lens 64f and the detector 65e. Although half the intensity is lost on the outgoing path and half on the incoming path, this technique is simpler and less expensive than using a polarizing beam splitter and quarter wave plate to eliminate these losses. However, target reflectivities are low, or available alignment laser powers are too low, this more involved technique can be used.

If the target 16 is very diffuse then the intensity distribution on the detector 65e is very similar to that of the alignment laser-produced spot on the target 16. If the reflectivity drops of quickly with angle there will be a bright spot within the image on the detector 65e. If the viewing angle is normal to the surface of the target 16, this bright spot will be centered within the image on the detector 65e. The intensity information from the detector 65e is provided to closed loop control circuitry (not shown) which drives xy tilt mechanisms 65g on steering mirror 64 to bring the bright spot to the center of the image on the detector 65e. By subsequently employing the xy tilt mechanisms 65g to maintain the spot at the center of the image received by detector 65e, the probe and impulse beams 28b and 28a are maintained normal to the surface of the target 16, which is the desired result.

Some materials, such as rolled aluminum, have different reflectivity angular distributions for the axis along a strip relative to the axis perpendicular to the strip. This may necessitate greater sensitivity along one axis compared to another. This can be accomplished by using an elliptical spot on the target 16 (minor axis in the direction of greater required sensitivity) and providing the lens 65f as one or more cylindrical lenses to image the orthogonal axis of the ellipse separately on to the detector 65e. The cylindrical lenses function to create a circular spot on the detector 65e.

The transfer function of a two detector polarizing interferometer 18 is shown in FIG. 5. For a given target 16 surface displacement (x-axis), the interferometer 18 generates a signal (y-axis) given by the illustrated sinusoidal curves. FIG. 5 shows the transfer functions for two photodetectors 42 that are 90° apart in phase, although it should be realized the system 10 may operate with one, two, or even more photodetectors 42. What should be evident from this transfer function is that the most sensitive, and hence the most desirable and optimum points of operation are at the maximum slopes, i.e., points E, C, F, D.

An interferometer may use vibrating mirrors or other moving parts to adjust or dither the reference leg of the interferometer so as to forge the system to operate at such points. However, this approach may not be desirable for all applications in that it adds to the overall complexity and cost of the system.

In accordance with a further aspect of this invention the system 10 operates at these optimum points, without the use of moving optical components, by an algorithmic technique that results in the triggering of the impulse laser 14 only at times when the signal received from the photodetector(s) 42 is optimum.

Figure 6:
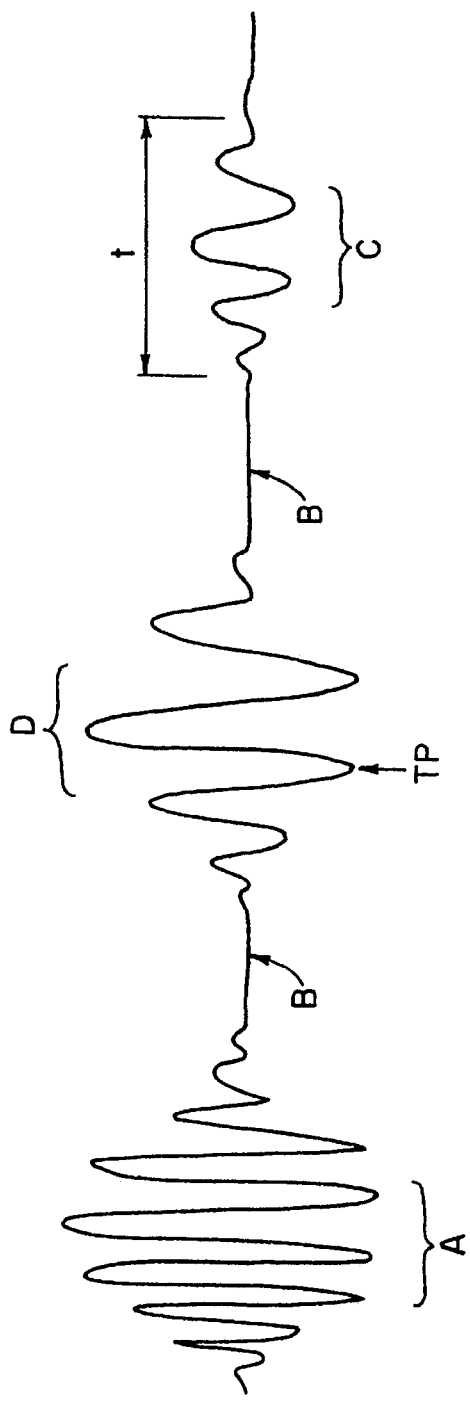
FIG. 6 illustrates exemplary received signals generated by the polarizing interferometer of FIG. 2, and is useful in describing a 'trigger-on-demand' mode of operation.

FIG. 6 shows a typical signal received from a target 16 (moving in this case, but static targets have a similar response). As shown, there are "bursts" of sinusoidal signals designated as A, D, and C, interspersed with regions B of little or no sensitivity (flat line). The bursts occur, typically, over a time (t) of two to four milliseconds.

The regions A, B and C represent 'poor' signal regions, while the region D represents a 'good' signal region, i.e., low frequency target motion and a high signal amplitude.

The poor region A exhibits a high signal amplitude, but also has a high frequency of target motion. The existence of the region A is usually due to target motion and, in most cases, regular environmental vibrations that cause oscillations of low frequency. It is important to note that these oscillations are not of the same frequency as the environmental vibrations, but instead represent the number of wavelengths per unit time received by the interferometer 18. For example, a low frequency, but very large amplitude, external vibration can cause the target 16 to move by many millions of wavelengths in a very short time. On the other hand, the same condition can be caused by a high frequency, but low amplitude vibration. If the frequency of these wavelengths reaches the useful data range (for example, 300 kHz to 2 MHz), then no subsequent filtering action can separate the desired signal from the external vibrations. The situation may be referred to as "frequency poisoning".

The existence of the regions B of FIG. 6 can be attributed to one or more of the following: (a) no return light, hence no interference, which can be caused by receiving a dark speckle from the target 16 (light and dark speckles are randomly distributed); and (b) no interference due to a lack of diode laser 22 coherence, which can be caused by instability in the laser operation or signal/reference leg path differences being larger than the coherence length of the diode laser 22.

The region C exhibits a low frequency of target motion, but also has a low signal amplitude. This can be due to a lack of contrast in the interference fringes or by an insufficient amount of returned light.

In the regions A, B and C of FIG. 6 any obtained data would not be acceptable, and it is thus desirable to inhibit the taking of data with the interferometer 18 during these times.

In accordance with this aspect of the invention the system 10 operates with an impulse laser 14 "trigger on demand"

(TOD) technique that triggers the impulse laser 14, and hence collects data, only during a period of reception of a "good" signal (i.e., region D of FIG. 6).

Figure 9:
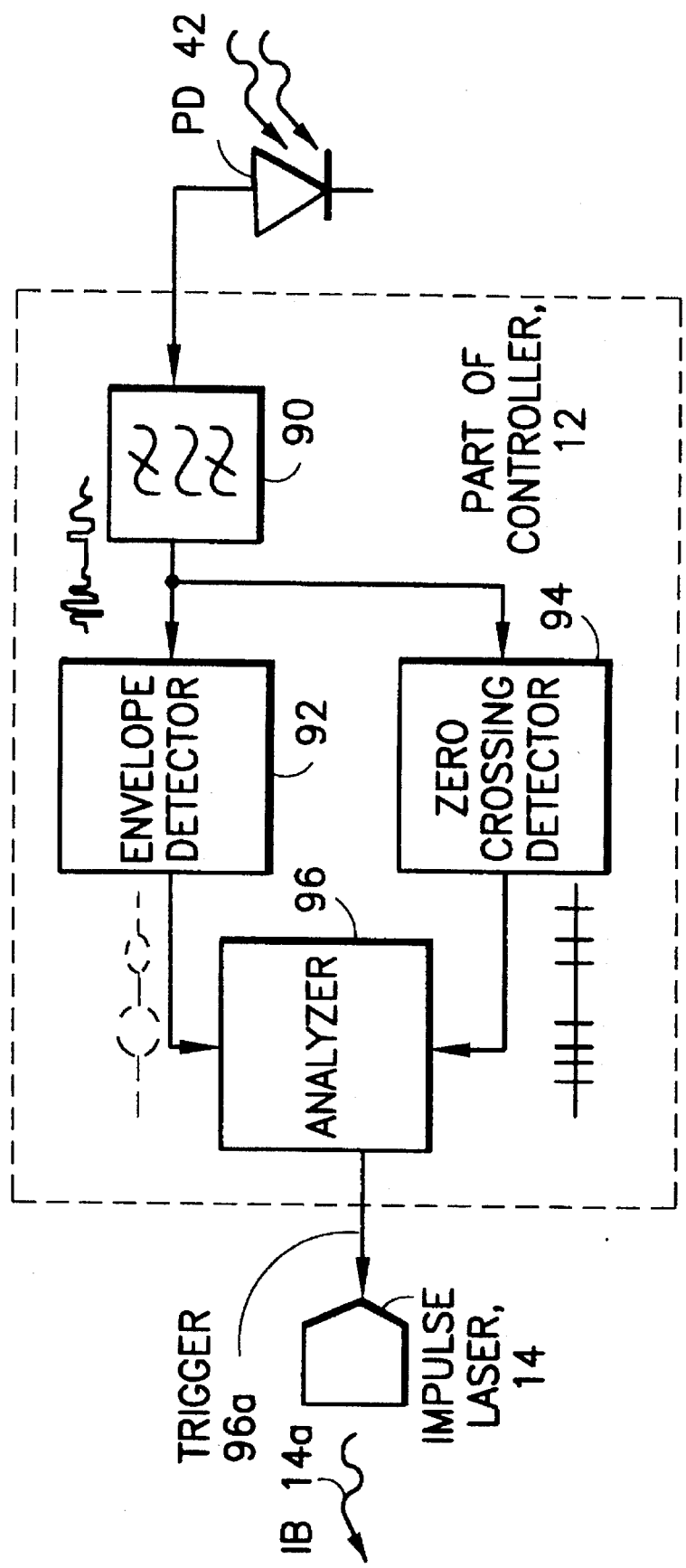
FIG. 9 is a block diagram showing a sub-system of the controller of FIG. 2 used for triggering the impulse laser of FIG. 2 at an optimum point on the transfer function of FIG. 5.

Referring to FIG. 9, the controller 12 includes a bandpass filter 90 that is coupled to the photodiode (PD) 42. When operating in the Rayleigh mode the desirable signals are generally in the range of approximately 1–5 MHz, while when operating in the Lamb mode the desirable signals are generally in the range of approximately 100 kHz to 1 MHz. The output of the filter 90 is connected to an envelope detector 92 and to a zero crossing detector 94. The envelope detector 92 determines the amplitude of the bursts received from the photodiode 42, while the zero crossing detector 94 detects the zero crossings and, hence, the frequency component of the sinusoidal bursts. An analyzer 96 monitors the output of the envelope detector 92 and the output of the zero crossing detector 94 to determine a condition wherein both the burst amplitude and frequency indicate that a 'good' burst is occurring. The occurrence of such a good burst indicates a lack of all or most of the undesirable conditions described in conjunction with the regions A, B and C or FIG. 6 (e.g., loss of laser diode coherence, unacceptable target motion, the reception of a dark speckle, etc.). The analyzer 96 then triggers the impulse laser 14 to initiate a measurement during the remaining period of the good burst. This trigger point (TP) is indicated in the region D of FIG. 6.

Not only, is-the trigger point initiated during the good burst, but the timing of the trigger may also be selected so that an expected elastic wave detection will occur at or near an optimum point on the sinusoidal signal.

By example, and referring also to FIG. 5, if the expected TOF is approximately ¼ of the period of the sinusoidal signal then the TP occurs at a point corresponding to point A in FIG. 5, which results in the launched elastic wave passing under the probe beam 28b at or about the optimum measurement point C on the sinusoid. Of course, any latencies in the operation of the impulse laser 14 are also considered, and the initiation of the trigger 96a is adjusted accordingly. Typical latencies are in the range of 100 μsec to 200 μsec.

It should be realized that the functions depicted in FIG. 9 may be executed wholly, or partially by a suitably programmed processing device.

Figure 14:
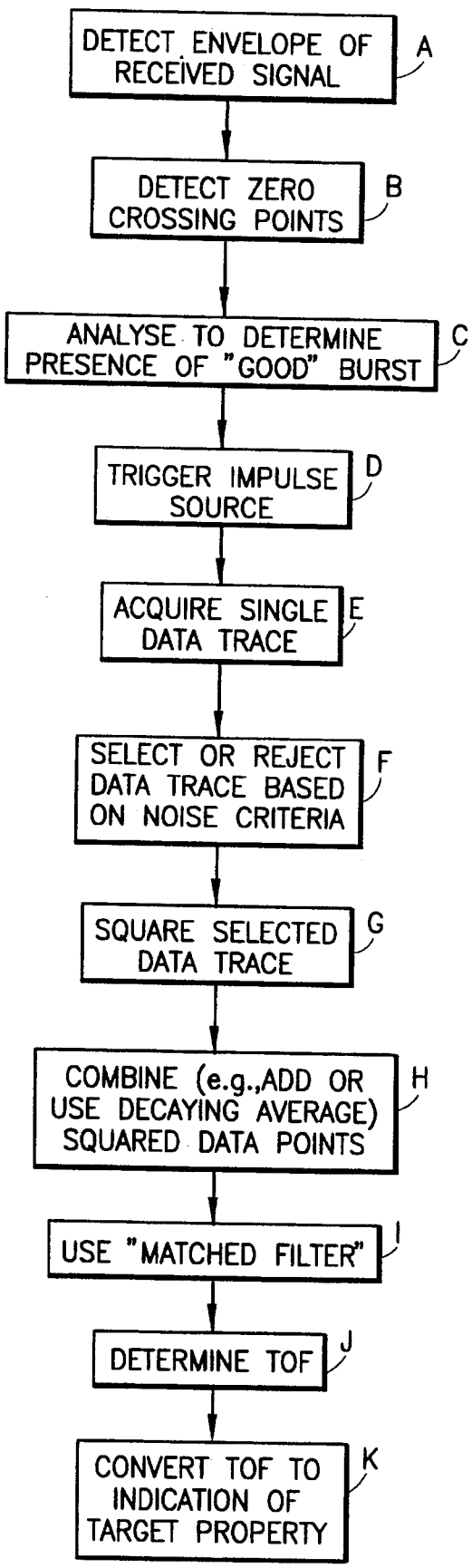
FIG. 14 is flow chart of a method of this invention.

Thus, and referring to FIG. 14, in accordance with a method of this invention there are performed the steps of (A) detecting the envelope of the received signal to determining the amplitude of the sinusoidal oscillations; (B) detecting zero crossing points of the sinusoidal oscillations identify the frequency of the burst; (C) analyzing the detected amplitude and the detected frequency to determine an occurrence of a good burst; and (D) triggering the impulse laser 14 at an appropriate time in order to collect data at the maximum slope operating points of the polarizing interferometer 18, i.e., points E, C, F, or D of FIG. 5.

Irrespective of how the impulse laser is triggered (i.e., steps A–D are preferred but not required), the signal processing of the received signal proceeds as follows: (E) acquiring a trace of signal vs. time; (F) accepting or rejecting the data based on criteria of allowable signal noise; (G) squaring the data; (H) accumulating similar data traces and combining them by adding the data, or by using techniques such as weighted averaging; (I) using a 'matched filter' to extract a feature of interest from the processed signal; (J) calculating the TOF from the 'matched filter'; and (K) converting the TOF to useful properties of the material (such as temperature, metallurgical status, etc.) by using predetermined calibration curves.

Figure 10A:
FIG. 10a is a cross-sectional view of a thin solid and illustrates, not to scale, an exemplary Lamb mode being supported by the solid.
Figure 10B:
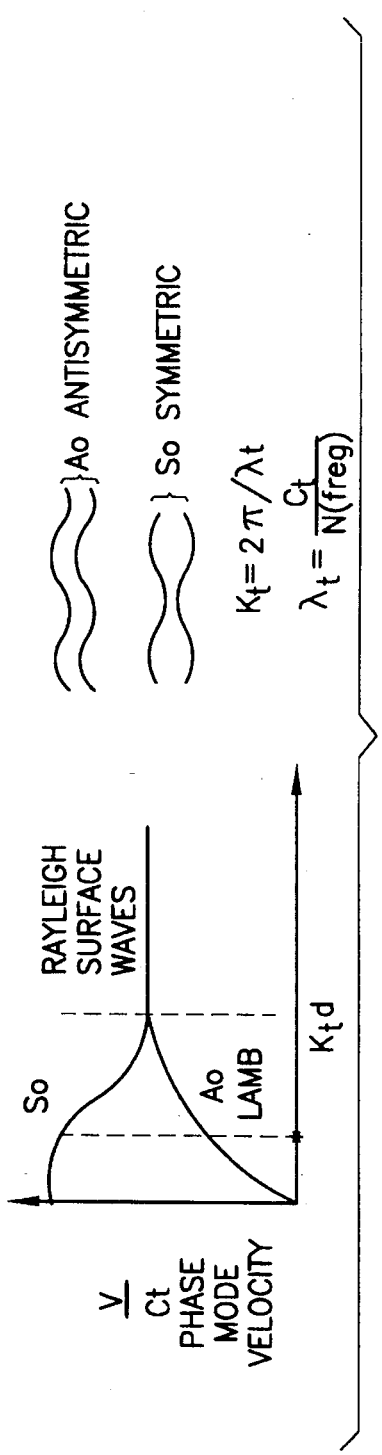
FIG. 10b is graph that plots shear mode velocity versus thickness for a solid, and shows the convergence of the dispersive $S_o$ and $A_o$ Lamb modes into Rayleigh surface waves.
Figure 10C:
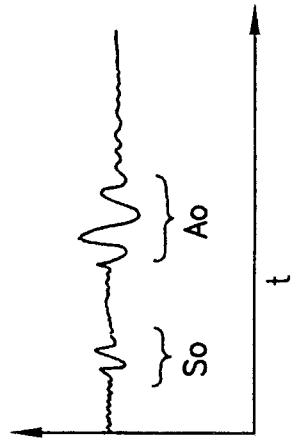
FIG. 10c is a graph that illustrates a difference in propagation velocity of the $S_o$ and the $A_o$ Lamb modes.

In this regard reference is now made to FIGS. 10a–10c and 11. The aforementioned Rayleigh waves are surface waves associated with relatively thick targets. In contradistinction, the Lamb waves are supported only in relatively thin targets (e.g., d=up to approximately 0.1"). As shown in FIG. 10b the Lamb waves are characterized by a symmetric mode ($S_o$) and an asymmetric or anti-symmetric mode ($A_o$). The $A_o$ mode is dispersive. The Lamb modes propagate through,the target in a waveguide-like fashion. The $S_o$ is typically more difficult to observe because it is relatively weak compared to the $A_o$ mode. As shown in FIG. 10c, these two modes travel with different velocities within the target. As the thickness of the target increases there is a smaller difference between the velocities until the Rayleigh regime (i.e., non-dispersive surface wave mode) is entered.

In accordance with an aspect of this invention the $S_o$ and $A_o$ Lamb modes are detected and are employed in combination to obtain the temperature of the target 1. That is, equations with two unknowns (thickness and temperature) are solved based on the $S_o$ and $A_o$ velocities which are detected in response to the application of the impulse beam 14a. One particularly useful application is in detecting the temperature of a thin substrate, for example a silicon substrate having a thickness in the range of approximately 200 to 400 micrometers. An embodiment of this application will be described below with reference to FIG. 12.

Figure 11A:
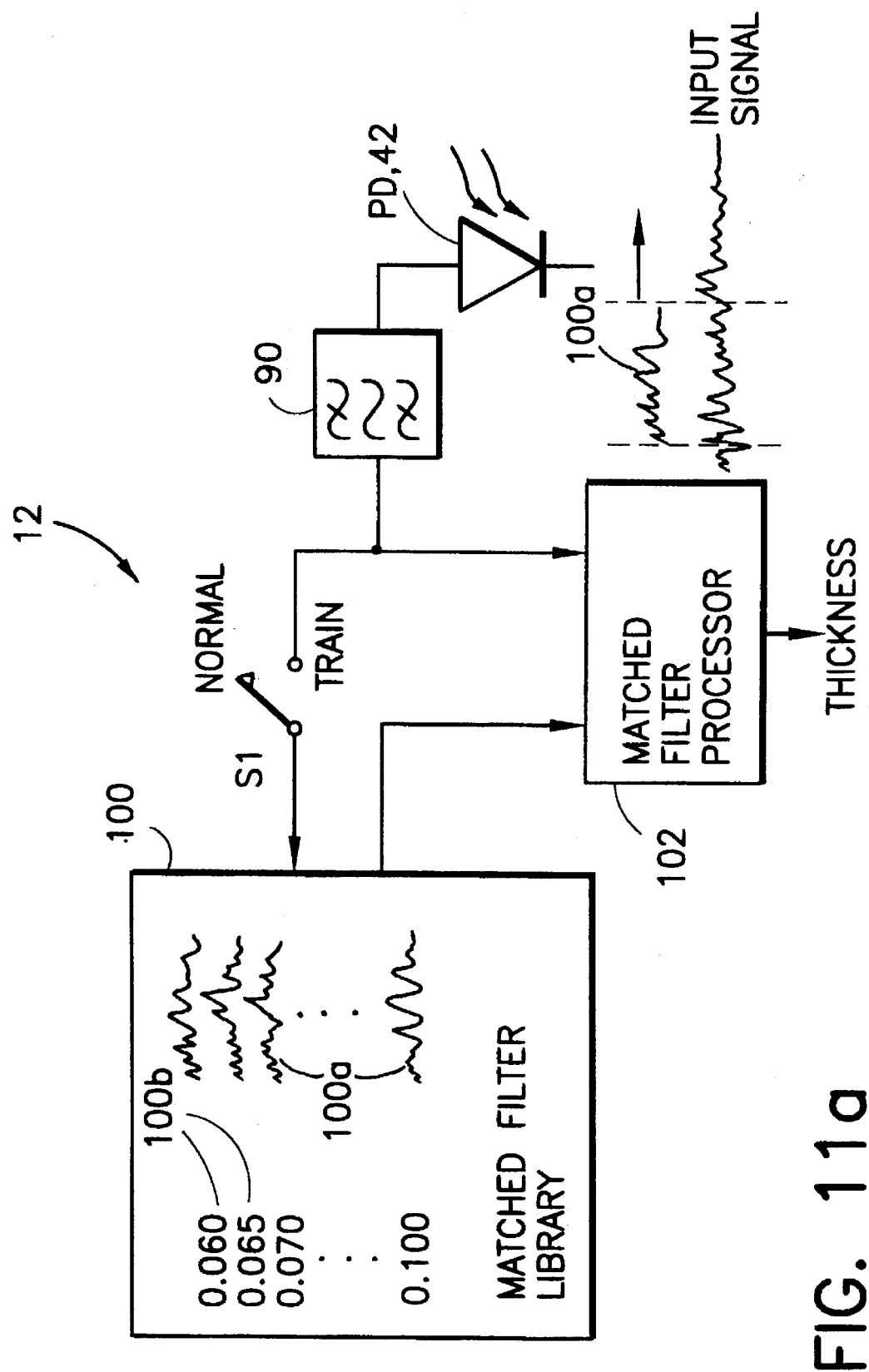
FIG. 11a is a block diagram showing a first embodiment of a signal processing sub-system of the controller of FIG. 2.

Reference is now made to FIG. 11a which shows a portion of the controller 12 in accordance with one embodiment of this invention. In this embodiment a matched filter library 100 is employed in conjunction with a matched filter processor 102 to determine the thickness of a substrate. As an example, for the Lamb mode case a plurality of wave templates or shapes 100a are digitized and stored during a training mode of operation using samples of predetermined thickness (100b). The stored shapes are each based on a plurality of measurements taken on a single sample. The measurements are preferably filtered and otherwise processed to eliminate noise and other artifacts of the measurement process. Each stored wave shape 100a thus represents an average of the plurality of measurements. The training mode is indicated schematically by the switch S1 being in a closed position. During the normal mode of operation the PD 42 output signal is applied to the matched filter processor 102 as an input signal. Individual ones of the stored shapes 100a are compared to the input signal to determine a best match through an autocorrelation technique (indicated by the arrow). The best match shape 100a is then correlated with its associated thickness 100b. Having determined the thickness of the sample, the temperature can be determined.

While a plurality of stored waveshapes 100a are preferred when operating in the Lamb regime, only a single filter shape is normally required when operating in the Rayleigh regime. Alternately, when operating in the Rayleigh regime a peak detection technique can be employed, as described in U.S. Pat. No. 5,286,313.

Figure 11B:
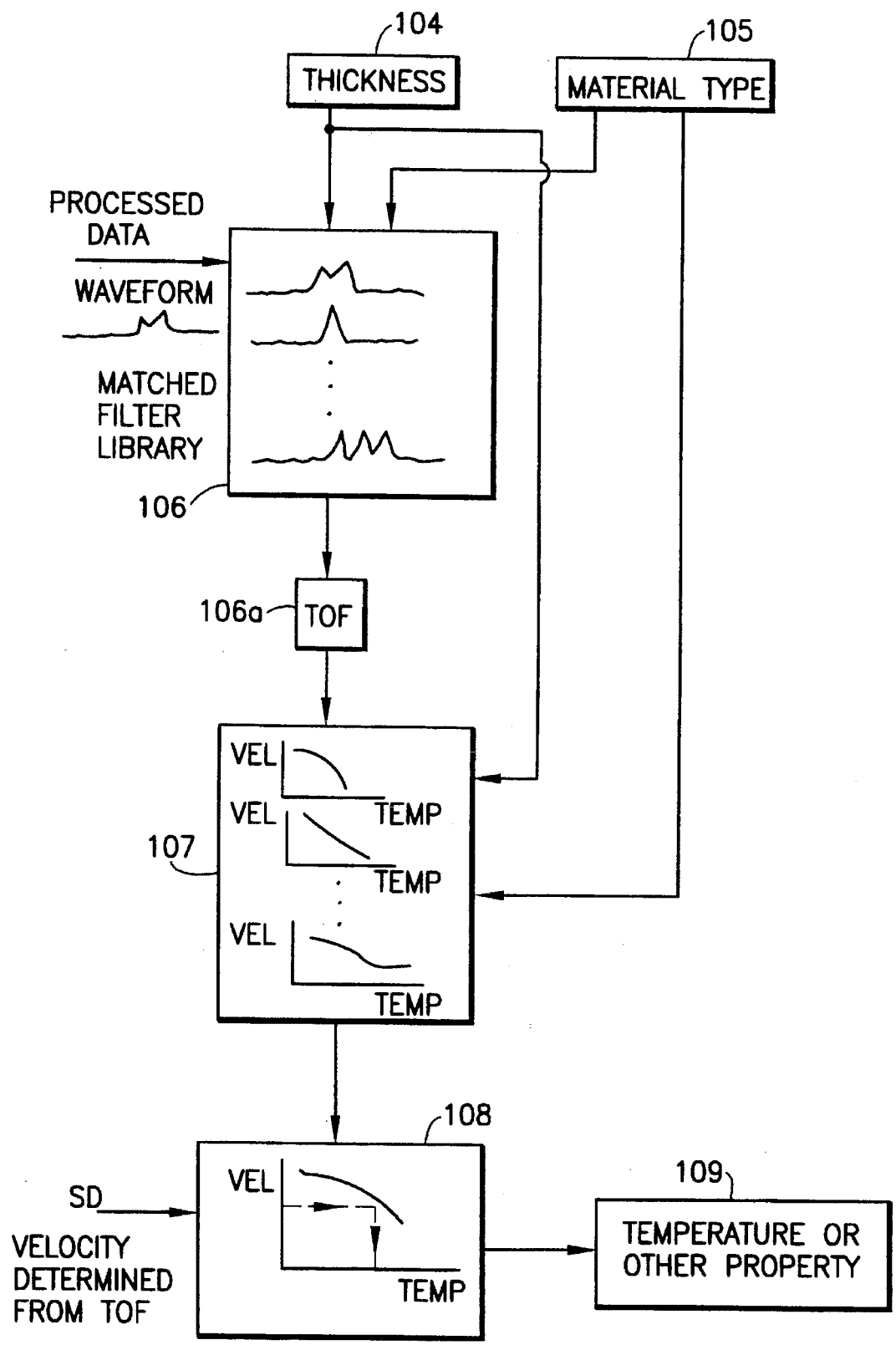
FIG. 11b is a block diagram showing a second embodiment of a signal processing sub-system of the controller of FIG. 2.

Reference is now made to FIG. 11b which illustrates a second signal processing embodiment, specifically a calibration technique for velocity measurements. In general, this is a method to convert the TOF measurements to velocity and then to, by example, temperature. This technique is especially applicable to thin targets, where Lamb modes are used and dispersive behavior is observed. Although temperature is used as an example, the method can be generalized for other material properties. Furthermore, although the TOF of the elastic wave is illustrated, this embodiment may be generalized to determine a time varying characteristic (e.g., frequency, phase, etc.) of the elastic wave.

The inputs to this signal processing embodiment may be manually or automatically generated. For example, the thickness of the target can be automatically inferred by the method described in FIG. 11a, or may be manually inserted from the user interface 12a.

Figure 1A:
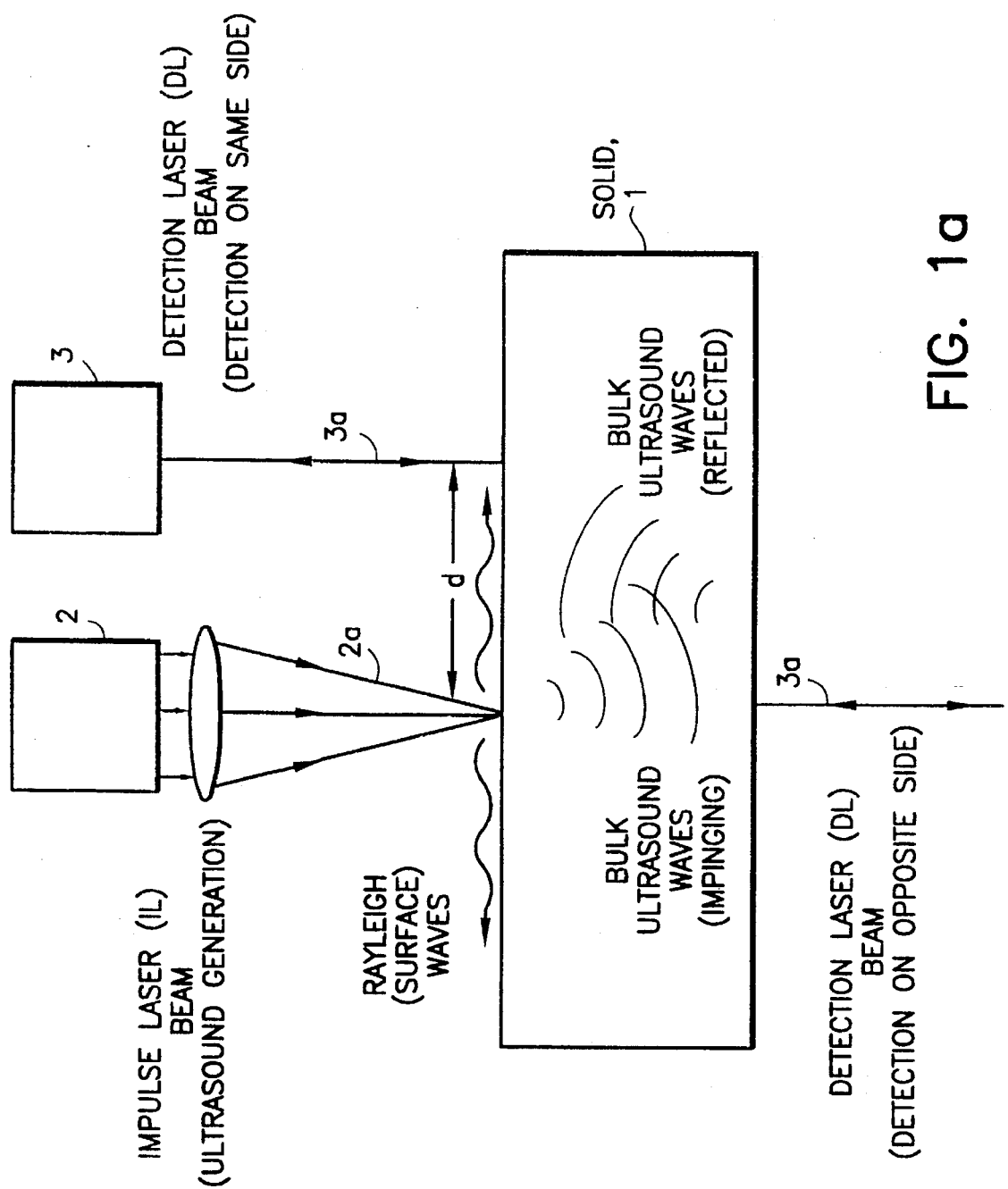

The inputs are the target thickness 104 and material type 105. The material type 105 may be, by example, the identification of an alloy. For a single sided configuration (see, for example, FIGS. 1a and 1b), the separation distance (SD) between the impulse beam 14a and the probe beam 28b may be provided as a constant. Already stored in the processor are the following: a library of "matched filters" 106 and a library of calibration curves 107. The library of calibration curves 107 may represent, by example, velocity vs. temperature (see, for example, FIG. 15) or, more generally, one or more ultrasonic pulse or elastic wave characteristics vs. material property (e.g., temperature). The thickness and material type inputs 104 and 105, respectively, are used to select one of the stored matched filters from library 106 and a calibration curve from the library 107. Having selected a corresponding matched filter from the library 106, the processed data waveform is then compared with the selected matched filter until a best match is obtained. This is a correlation operation that yields the TOF 106a. The TOF 106a is then converted to the velocity of the elastic wave based on the SD.

Then, using the calibration curve selected from library 107 as a function of the thickness 104 and material type 105 inputs, the temperature or some other material property is determined in block 108 and is output as a result 109.

Figure 12:
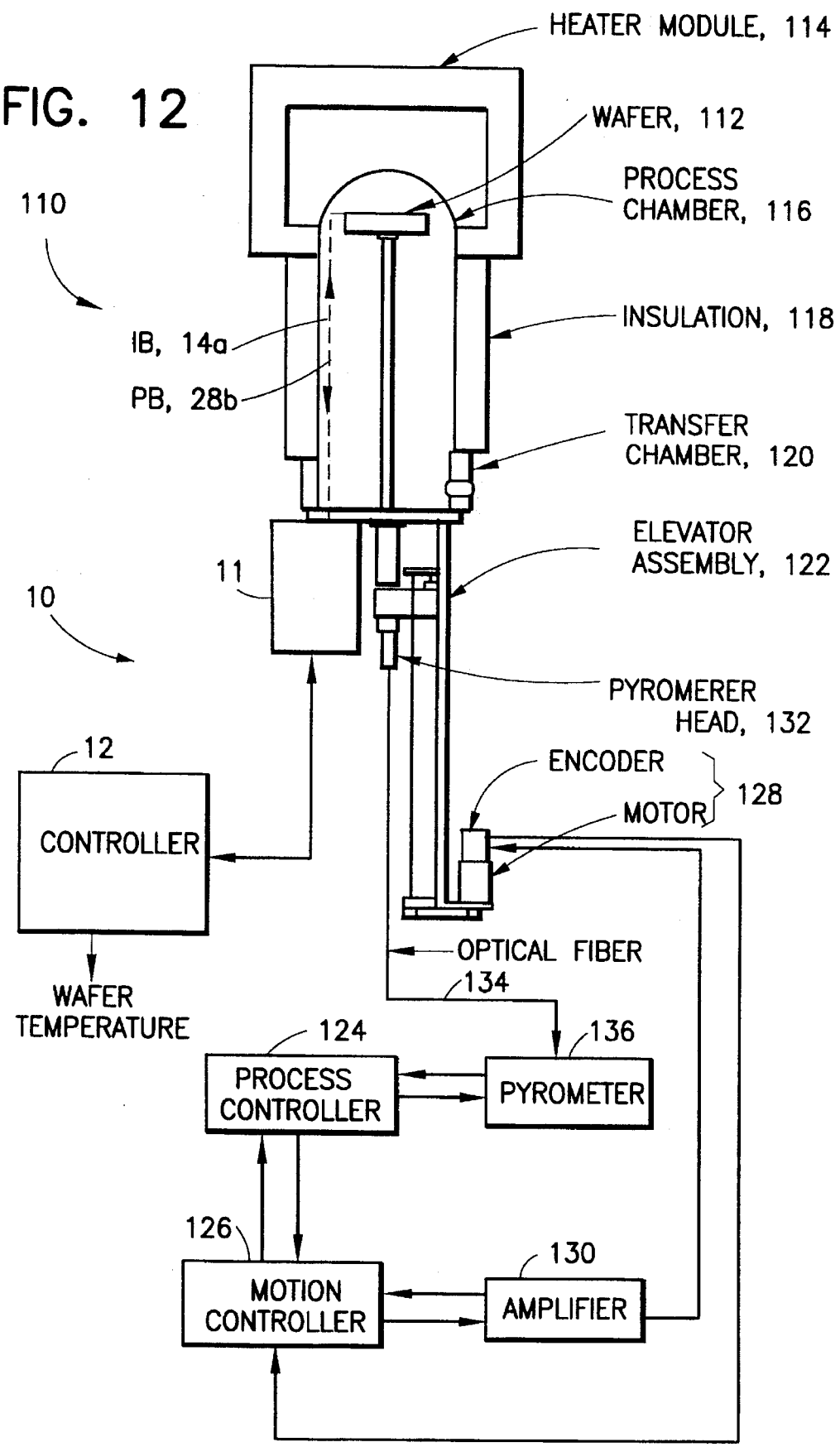
FIG. 12 is a cross-sectional view of a rapid thermal processor (RTP) system that is constructed and operated in accordance with this invention.

An application of the Lamb mode processing technique of this invention is illustrated in FIG. 12. This figure generally shows a rapid thermal processing (RTP) system 110 which is used for the thermal processing of a silicon wafer 112. A heater module 114 surrounds a portion of a process chamber 116 which is covered by a layer of thermal insulation 118. A lower transfer chamber 120 enables the wafer 112 to be loaded into and extracted from the process chamber 116. After being loaded an elevator assembly 122 is used to raise and lower the wafer 112 within the process chamber 116. A very rapid heating (e.g., 50°–100°/sec) of the wafer 112 occurs during this process. Also shown in FIG. 12 are various other system components such as a process controller 124, an elevation motion controller 126, and an associated motor/encoder 128 and amplifier 130 for raising and lowering the elevator assembly 122. A pyrometer head 132 is connected via an optical fiber 134 to a pyrometer 136 for measuring, by emissivity, the temperature within the process chamber 116. The pyrometer 136 is interfaced to the process controller 124 to close the temperature control loop.

In accordance with the invention the RTP system further includes the laser ultrasonics materials analysis system 10 of this invention. The head 11 is disposed so as to direct the impulse beam 14a and the probe beam 28b onto a surface of the wafer 112 during the thermal processing of the wafer. Because of the thinness of the silicon wafer 112 crystalline nature of the silicon wafer 112 the S° Lamb the Lamb mode of operation (FIG. 11b) is preferably utilized,to determine the wafer temperature. Due to the mode is more apparent because there is less background noise than would be found in, for example, a metal substrate of the same dimensions. This enables temperature measurements of the wafer 112 with an accuracy equal to or less than ±5° F. This temperature measurement occurs without using the emissivity of the silicon wafer, which would be difficult to accurately measure within the high ambient temperature of the process chamber 116.

This is an important application of the invention as it avoids processing errors which can result in the destruction of the wafer 112. As larger wafers come into use (e.g., 8" to 12" wafers) the expense of a single wafer, which may have a very significant production cost associated therewith, makes an accurate measurement of wafer temperature very important.

Figure 13:
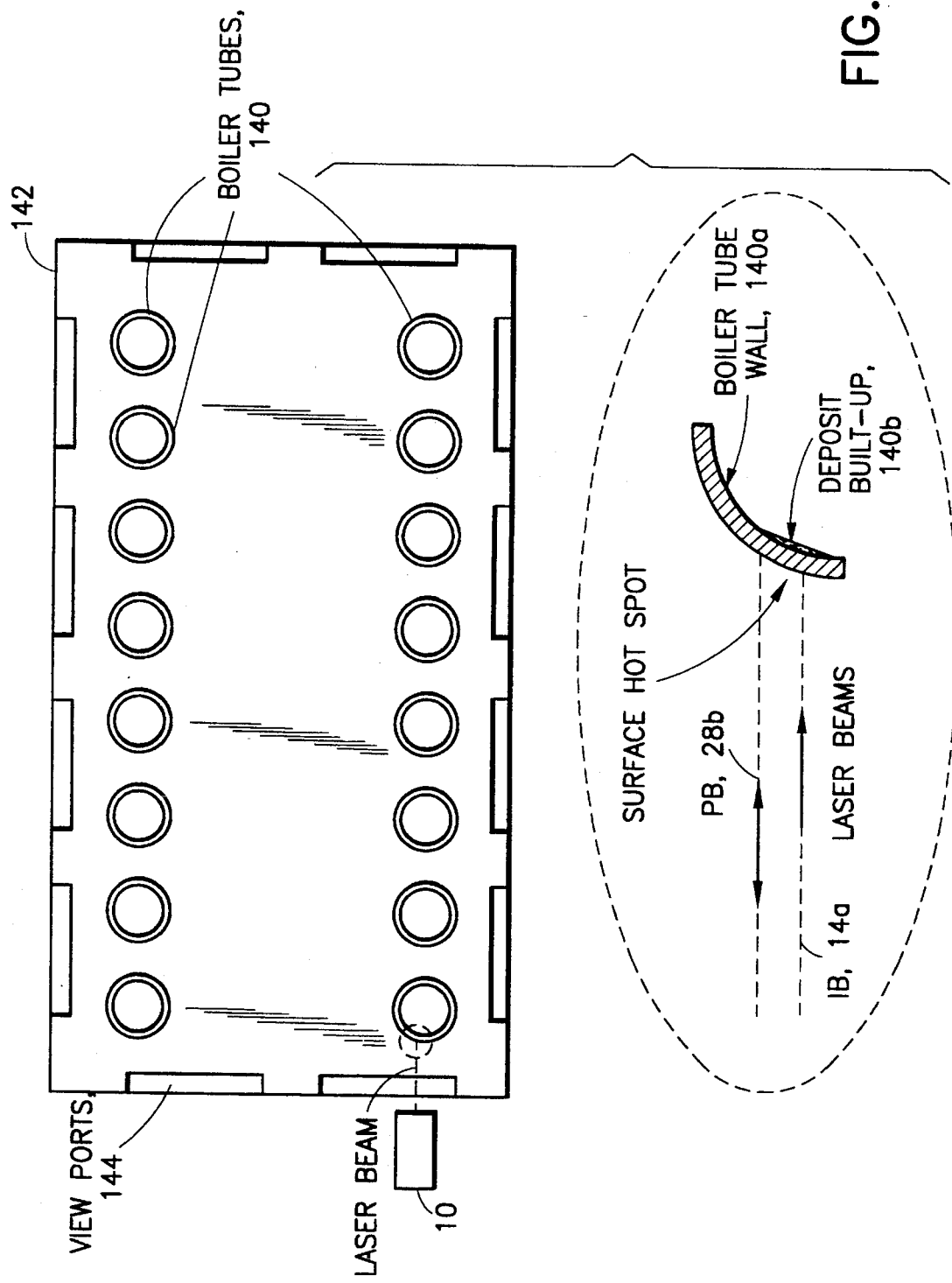

FIGS. 13a and 13b show another exemplary application of the system 10. In FIGS. 13a and 13b the system 10 is used to monitor the surface temperature of boiler tubes 140 within a furnace 142. Such an arrangement is often found within a petrochemical refinery. One or more view ports 144 enable optical access to the boiler tubes 140. As shown in the enlarged detail, the IB 14a and PB 28b are directed onto the surface of a boiler tube wall 140a. If a deposit build up (shown generally as 140b) occurs on the inner surface of the boiler tube wall 140a, a hot spot is created on the outer surface. The presence of such a hot spot is undesirable in that it can eventually lead to metal fatigue and the failure of the affected boiler tube 140. Since the boiler tubes normally carry a pressurized heated volatile fluid, such a failure can be catastrophic.

The use of the system 10 enables a remote (non-contact) and very accurate reading of surface temperature along the boiler tube outer walls and thus enables a detection of surface hot spots before metal failure occurs.

Figure 15:
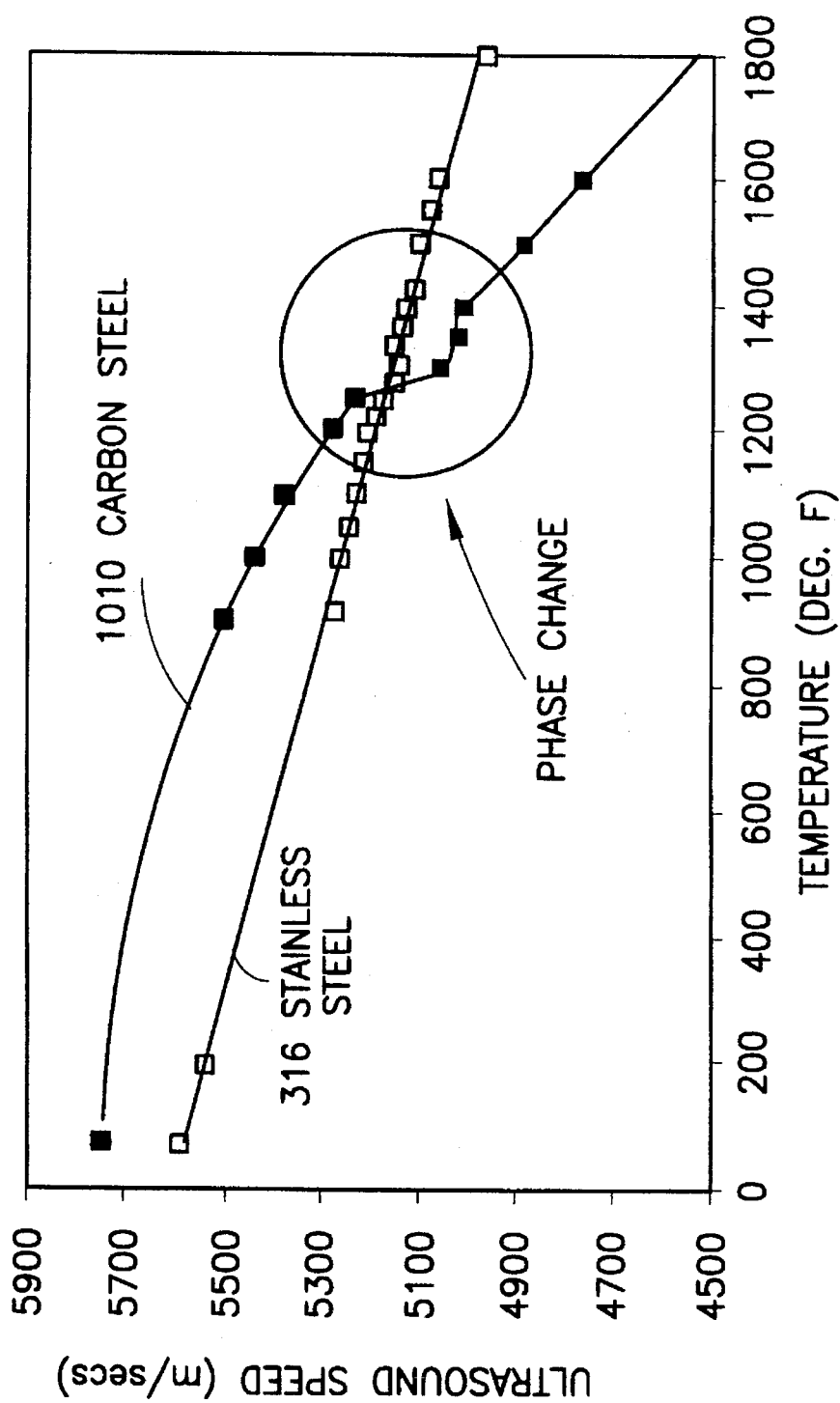
FIG. 15 is a graph illustrating a phase change that occurs in the making of steel, and which is detectable by the system of the invention.

An exemplary, but certainly not exhaustive list of other applications that may benefit from the remote, contactless temperature measurement system of this invention include the heat treating industry (measurement of internal and surface temperature of steel, aluminum, etc.); the carburizing industry (measurement and control of carburization depth and surface hardness); phase change processing (as shown in FIG. 15, the detection of onset and completion of phase changes during steel processing); and nondestructive inspection (detection of internal flaws, cracks, and voids in structures). In the flaw detection application additional signal peaks are observed which arise from internal flaws within a structure (such as bridge support) under test. Another application of interest is the process control of paper, i.e. mechanical strength, water content, etc.

With regard to flaw detection, it is well known to use high frequency ultrasound, such as that derived from a piezoelectric transducer, for detecting small cracks and flaws during target inspection. It is known to use a mode locked laser to generate ultrasonic waves at frequencies as high as 100 MHz. It is also known that in addition to the detection of small flaws, the mode-locked laser operation can generate very narrow band ultrasound (not necessarily high frequency).

This is exploited in the system 10 to substantially improve the SNR of a measurement by reducing the electronics bandwidth. Particularly in the measurement of thin targets (for example, under 0.1" for metals) the Lamb modes of the target are dispersive, which implies that the thickness of the target affects the received pulse. This dispersive behavior is problematic since it necessitates the prior knowledge of the thickness. However, this behavior disappears for thicker targets or for higher frequency ultrasound. In other words, theory predicts that the waves are not dispersive for high values of the product of frequency and thickness. Therefore, for very thin targets the high frequency ultrasound may be used to avoid the dispersive characteristics of the waves.

It is pointed out that there are many ways of analyzing the received signals. As was described previously, one technique is to first detect the arrival of the wave (peak detection) and then from the Time-Of-Flight (TOF) calculate the velocity by knowing the distance or the path length. The determined elastic wave velocity correlates with many properties of the target, such as temperature, metallurgical status, etc. However, the velocity measurement is not the only suitable method for analyzing the signal.

In accordance with a further aspect of this invention any time varying characteristic of the received elastic wave may be used to monitor various material properties, such as carbon content, case depth, grain size, etc. Exemplary time varying characteristics include the frequency of the received elastic wave, the phase of the received elastic wave, and an amplitude modulation of the envelope of the received elastic wave. Methods such as Fast Fourier Transformations, Wavelets, etc. are used in the system 10 to measure the time varying content, such as frequency characteristics, of the received elastic wave so as to correlate the measured time varying content with one or more material properties of interest.

Having thus described the invention, it will be appreciated that a number of modifications may be made to the disclosed embodiments. As an example, although the trigger on demand technique has been previously described with respect to FIGS. 5, 6, 9 and 14, it should be realized that it is also within the scope of the invention to employ a mechanism, such as a piezoelectric actuator, to mechanically dither the reference leg to provide an active stabilization. Furthermore, the active stabilization of the reference leg can be used in conjunction with the trigger on demand technique.

Also by example, it is within the scope of this invention to eliminate a thickness test altogether when determining a material's properties. More particularly, when thick targets are being investigated (e.g., thicker than 0.125") and bulk waves are being used, then there is a need for prior sided (reflected waves from opposite side) and double sided (one pass through target) configurations. In both of these cases the travel distance of the elastic wave needs to be known in order to calculate the velocity from the TOF measurements.

Figure 17:
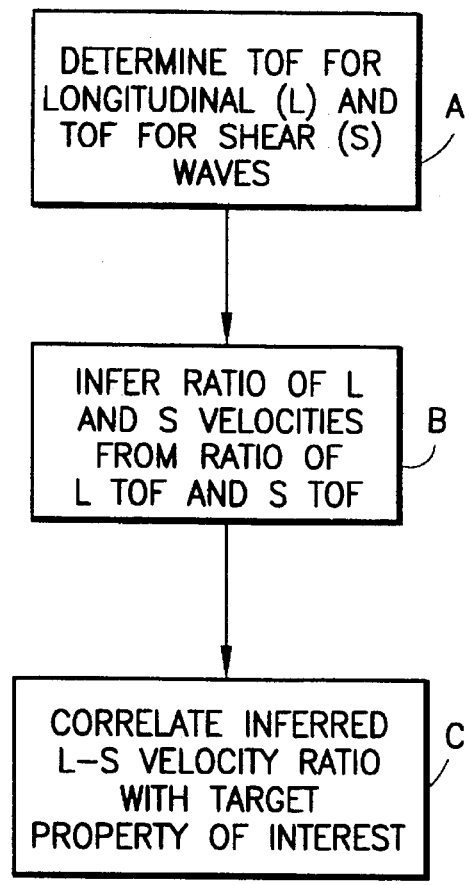
FIG. 17 is a flow chart of a method of this invention that employs the determination of the TOFs of both longitudinal and shear waves.

As is illustrated in the flow chart of FIG. 17, a method for determining the travel distance, without knowing the thickness a priori, is to generate an elastic wave in the target and to then detect the arrival of both Longitudinal (L) and Shear (S) waves. For metals, the latter travel with almost half the speed of the former. Therefore these waves arrive at different points in time and can thus be detected separately. After both of the waves are received and detected (Block A), the ratio of the determined L and S TOFs are used to infer the ratio of the L and S velocities (Block B). The travel path drops out of this calculation, since it is the same for both waves. Therefore, instead of correlating the velocity of each wave with the target properties, the ratio of the L and S velocities is correlated with a target property of interest (Block C), thereby avoiding any thickness uncertainty.

It should be noted that this capability is an important feature of the system 10, which uses interferometric detection and can therefore monitor both E and S waves. Conventional contact piezoelectric transducers used in ultrasonic inspections lack this capability, and special transducers are used for each wave set.

Thus, while the invention has been particularly shown and described with respect to preferred embodiments thereof, it will be understood by those skilled in the art that changes in form and details may be made therein without departing from the scope and spirit of the invention. Further by example, the use of a diode detection laser is not mandatory for the novel signal processing techniques that were described previously, and neither is the use of a laser as the source of impulse energy to launch elastic waves within a sample.

What is claimed is:

1. A system for determining a characteristic of a target, comprising:

means for launching an elastic wave within the target;

an interferometer for detecting a displacement of a surface of the target in response to said launched elastic wave;

means, responsive to said detected displacement, for determining a time of flight of said elastic wave within the target; and means for correlating the determined time of flight with a characteristic of the target, wherein said interferometer includes at least one photodetector, and wherein said correlating means is comprised of:

means for detecting a waveshape of a signal output from said photodetector; and matched filter processing means comprising means for storing a plurality of predetermined waveshapes, each of said plurality of predetermined waveshapes corresponding to a different target thickness; means for comparing said detected waveshape to said stored plurality of predetermined waveshapes; and means for correlating a thickness of the target with a predetermined thickness that is associated with a selected one of said stored plurality of waveshapes that best matches said detected waveshape.

2. A system for determining a characteristic of a target, comprising:

means for launching an elastic wave within the target;

an interferometer including at least one photoresponsive detector for indicating a displacement of a surface of the target in response to the launched elastic wave;

signal processing means, responsive to said detected displacement, for determining a time varying characteristic of the elastic wave within the target and for relating the determined time varying characteristic with a property of interest of the target, wherein said signal processing means is comprised of:

means for determining a waveshape of a signal output from said detector;

matched filter processing means comprising means for storing a plurality of predetermined waveshapes;

calibration curve processing means comprising means for storing a plurality of calibration curves each relating an elastic wave time varying characteristic to a property of interest of the target;

means for selecting one of said stored plurality of predetermined waveshapes based on a thickness of the target and on a type of material that comprises the target;

means for determining a time varying characteristic of the determined waveshape in cooperation with the selected one of the stored plurality of predetermined waveshapes; and means for relating the determined time varying characteristic of the detected waveshape with the property of interest of the target in cooperation with one of the stored plurality of calibration curves.

* * * * *